US011147783B2

(12) United States Patent
Stott et al.

(10) Patent No.: US 11,147,783 B2
(45) Date of Patent: Oct. 19, 2021

(54) USE OF CANNABINOIDS IN THE TREATMENT OF EPILEPSY

(71) Applicant: GW Research Limited, Cambridge (GB)

(72) Inventors: Colin Stott, Cambridge (GB); Nicholas Jones, Cambridge (GB); Robin Williams, Egham (GB); Benjamin Whalley, London (GB)

(73) Assignee: GW Research Limited, Cambridge (GB)

( * ) Notice: Subject to any disclaimer, the term of this patent is extended or adjusted under 35 U.S.C. 154(b) by 0 days.

(21) Appl. No.: 15/751,563

(22) PCT Filed: Jul. 29, 2016

(86) PCT No.: PCT/GB2016/052340
§ 371 (c)(1),
(2) Date: Feb. 9, 2018

(87) PCT Pub. No.: WO2017/025712
PCT Pub. Date: Feb. 16, 2017

(65) Prior Publication Data
US 2018/0228751 A1 Aug. 16, 2018

(30) Foreign Application Priority Data
Aug. 10, 2015 (GB) .................................... 1514079

(51) Int. Cl.
| *A61K 31/192* | (2006.01) |
| *A61K 45/06* | (2006.01) |
| *A61K 31/05* | (2006.01) |
| *A61K 36/185* | (2006.01) |
| *A61P 25/08* | (2006.01) |

(52) U.S. Cl.
CPC ............ *A61K 31/192* (2013.01); *A61K 31/05* (2013.01); *A61K 36/185* (2013.01); *A61K 45/06* (2013.01); *A61P 25/08* (2018.01)

(58) Field of Classification Search
CPC .... A61K 31/05; A61K 31/192; A61K 36/185; A61K 45/06; A61P 25/08
See application file for complete search history.

(56) References Cited

U.S. PATENT DOCUMENTS

| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,730,911 B2 | 8/2017 | Verzura et al. |
| 9,949,936 B2 | 4/2018 | Guy et al. |
| 9,949,937 B2 | 4/2018 | Guy et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,092,525 B2 | 10/2018 | Guy et al. |
| 10,111,840 B2 | 10/2018 | Guy et al. |
| 10,137,095 B2 | 11/2018 | Guy et al. |
| 2004/0110828 A1 | 6/2004 | Chowdhury et al. |
| 2005/0266108 A1* | 12/2005 | Flockhart ............. C07D 311/80 424/774 |
| 2006/0039959 A1 | 2/2006 | Wessling |
| 2007/0060638 A1 | 3/2007 | Olmstead |
| 2008/0119544 A1 | 5/2008 | Guy et al. |
| 2008/0188461 A1 | 8/2008 | Guan |
| 2009/0264063 A1 | 10/2009 | Tinsley et al. |

(Continued)

FOREIGN PATENT DOCUMENTS

| CA | 2737447 | 10/2012 |
| CA | 2859934 | 3/2016 |

(Continued)

OTHER PUBLICATIONS

[No Author Listed] "Cannabidiol Therapy for Aicardi Syndrome" Aug. 2014, 4 pages.
[No Author Listed], Cover and Table of Contents, J Pharmacology and Exp Therapeutics, Feb. 2010, 332(2), 4 pages.
Alger, "Not Too Excited? Thank Your Endocannabinoids," Neuron., Aug. 2006, 51(4):393-395.
American Epilepsy Society, Three Studies Shed New Light on the Effectiveness of Cannabis in Epilepsy, Oct. 14, 2014, 2 pages.
Ames et al., "Anticonvulsant effect of cannabidiol," S. Afr Med. J., Jan. 1986, 69(1):14.

(Continued)

*Primary Examiner* — Kara R McMillian
(74) *Attorney, Agent, or Firm* — Cooley LLP

(57) ABSTRACT

The present invention relates to the use of a therapeutically effective amount of cannabidiolic acid (CBDA) in the treatment of epilepsy. In one embodiment the CBDA is used in the treatment of generalised seizures, preferably tonic-clonic seizures. Preferably the CBDA used is in the form of a botanical drug substance in which the CBDA content is greater than 60%, and most preferably, it is a highly purified extract of *cannabis* such that the CBDA is present at greater than 95%, through 96% and 97% to most preferably, greater than 98% of the total extract (w/w) and the other components of the extract are characterised. In particular the cannabinoids tetrahydrocannabinol (THC) or tetrahydrocannabinol acid (THCA) have been substantially removed. Alternatively, the CBDA may be synthetically produced.

19 Claims, 6 Drawing Sheets

(56) References Cited

U.S. PATENT DOCUMENTS

| | | |
|---|---|---|
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0335590 A1 | 11/2015 | Whalley et al. |
| 2015/0343071 A1 | 12/2015 | Vangara |
| 2015/0359755 A1 | 12/2015 | Guy et al. |
| 2015/0359756 A1 | 12/2015 | Guy et al. |
| 2016/0000843 A1* | 1/2016 | Lowe .............. A61K 31/352 424/774 |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0338931 A1 | 11/2018 | Guy et al. |
| 2019/0083418 A1 | 3/2019 | Guy et al. |

FOREIGN PATENT DOCUMENTS

| | | | |
|---|---|---|---|
| CN | 101040855 | 9/2007 | |
| CN | 103110582 | 5/2013 | |
| DE | 102012-105063 | 12/2013 | |
| EP | 2448637 | 5/2012 | |
| GB | 2384707 | 8/2003 | |
| GB | 2434097 | 7/2007 | |
| GB | 2434312 | 7/2007 | |
| GB | 2450753 | 1/2009 | |
| GB | 0911580.9 | 7/2009 | |
| GB | 2456183 | 7/2009 | |
| GB | 2471523 | 1/2011 | |
| GB | 2478595 | 9/2011 | |
| GB | 2479153 | 10/2011 | |
| GB | 2485291 A * | 5/2012 | ............ A61K 31/352 |
| GB | 2471565 | 7/2012 | |
| GB | 2478072 | 12/2012 | |
| GB | 2478074 | 12/2012 | |
| GB | 2492487 | 1/2013 | |
| GB | 2487712 | 10/2015 | |
| WO | WO 2002/064109 | 8/2002 | |
| WO | WO 2003/099302 | 12/2003 | |
| WO | WO 2004/016246 | 2/2004 | |
| WO | WO 2004/016277 | 2/2004 | |
| WO | WO 2006/054057 | 5/2006 | |
| WO | WO 2006/133941 | 12/2006 | |
| WO | WO 2007/083098 | 7/2007 | |
| WO | WO 2007/138322 | 12/2007 | |
| WO | WO 2008/019146 | 2/2008 | |
| WO | WO 2008/094181 | 8/2008 | |
| WO | WO 2008/129258 | 10/2008 | |
| WO | WO 2008/144475 | 11/2008 | |
| WO | WO 2008/021394 | 12/2008 | |
| WO | WO 2008/146006 | 12/2008 | |
| WO | WO 2009/007697 | 1/2009 | |
| WO | WO 2009/007698 | 1/2009 | |
| WO | WO 2009/020666 | 12/2009 | |
| WO | WO 2011/001169 | 1/2011 | |
| WO | WO 2011/121351 | 10/2011 | |
| WO | WO 2012/033478 | 3/2012 | |
| WO | WO 2012/093255 | 7/2012 | |
| WO | WO 2013/032351 | 3/2013 | |
| WO | WO 2015/142501 | 9/2015 | |
| WO | WO 2015/184127 | 12/2015 | |
| WO | WO 2015/193667 | 12/2015 | |
| WO | WO 2015/193668 | 12/2015 | |
| WO | WO 2016/059405 | 4/2016 | |
| WO | WO 2016/084075 | 6/2016 | |
| WO | WO 2016/118391 | 7/2016 | |
| WO | WO 2016/147186 | 9/2016 | |
| WO | WO 2016/022936 | 11/2016 | |
| WO | WO 2016/199148 | 12/2016 | |
| WO | WO 2017/168138 | 10/2017 | |
| WO | WO 2018/002636 | 1/2018 | |
| WO | WO 2018/002637 | 1/2018 | |
| WO | WO 2018/037203 | 3/2018 | |

OTHER PUBLICATIONS

Arain et al., "Pregabalin in the Management of Partial Epilepsy," Neuropsychiatr Dis Treat., Aug. 2009, 5:407-413.

Arzimanoglou et al., "All children who experience epileptic falls do no necessarily have Lennox-Gastaut syndrome . . . but many do," Epileptic Discord, 2011, 13:S3-S13.

Arslan and Tirnaksiz, "Self-emulsifying Drug Delivery Systems," FABAD J Pharm Sci, 2013,38(1): 55-64.

AU Third Party Observations for Application No. AU2012314129, dated Mar. 19, 2015, 51 pages.

Avoli et al., "Cellular and molecular mechanisms of epilepsy in the human brain," Prog Neurobiol., 2005, 77(3):166-200.

Bakhsm, "Key Attributes of TKDL," Miftaah-al-Khazaain, 1930, 607-608 (with English translation).

Bancaud et al., "Proposal for Revised Clinical and Electroencephalographic Classification of Epileptic Seizures," Epilepsia, Aug. 1981, 22(4):489-501.

Barker-Haliski et al, "How Clinical Development Can, and Should. Inform Translational Science," Neuron, Nov. 2014, 84: 582-593.

Benowitz et al., "Metabolic and Psychophysiologic studies of cannabidiol hexobarbital interaction," Clin Pharmacol Ther., 1980, 28(1):115-120.

Bertram, "The Relevance of Kindling for Human Epilepsy," Epilepsia, Apr. 2007, 48(Suppl. 2):65-74.

Bhatt et al., "Indigenous Plants in Traditional Healthcare System in Kedarnath Valley of Western Himalaya," Indian J Tradit Knowl., Apr. 2008, 7(2):300-310.

Bhattacharyya et al., "Modulation of mediotemporal and ventrostriatal function in humans by Delta9-tetrahydrocannabinol: a neural basis for the effects of *Cannabis sativa* on learning and psychosis," Arch Gen Psychiatry., 2009, 66:442-451.

BipolarHealthGroup.org [online], "Charlotte's Web Hemp Remedy," Bipolar Health Group, available on or before Sep. 6, 2017, retrieved on May 21, 2018, URL <http:/bipolarhealthgroup.org/index.php/charlottes-web-hemp-remedy/>, 6 pages.

Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.

Bostanci et al., "The effects of octanol on penicillin induced epileptiform activity in rats: An in vivo study," Epilepsy Res., Jul. 27, 2006, 71(2-3):188-194.

(56) References Cited

OTHER PUBLICATIONS

Braida et al., "Post-ischemic treatment with cannabidiol prevents electroencephalographic flattening, hyper locomotion and neuronal injury in gerbils" Neuroscience Letters., 2003, 346:61-64.
Brust et al., "Marijuana use and the risk of new onset seizures," Trans Am Clin Climatol Assoc., 1992, 103:176-181.
Carlini et al., "Hypnotic and Antiepileptic Effects of Cannabidiol," J Clin Pharmacol., Aug.-Sep. 1981, 21(8-9 Suppl):417S-427S.
Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.
Charlotte's Web [online], "When to Expect Results from CW Hemp Oil", Mar. 13, 2017, retrieved on May 21, 2018, URL https://www.cwhemp.com/blog/expecting-results-from-hemp, 6 pages.
Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.
ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennox-gastaut-syndrome, 10 pages.
Chiron and Dulac, "The Pharmacologic Treatment of Dravet Syndrome," Epilepsia, 2011, 52(Suppl. 2): 72-75.
Chiu et al., "The Influence of Cannabidiol and Δ9-Tetrahydrocannabinol on Cobalt Epilepsy in Rats," Epilepsia., 1979, 20:365-375.
Conry et al., "Clobazam in the treatment of Lennox-Gastaut syndrome," Epilepsia, May 2009, 50(5): 1158-1166.
Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.
Consroe et al., "Anticonvulsant drug antagonism of $\Delta^9$tetrahydrocannabinol-induced seizures in rabbits," Res Commun Chem Pathol Pharmacol., Jan. 1977, 16(1):1-13.
Consroe et al., "Anticonvulsant Interaction of Cannabidiol and Ethosuximide in Rats," J. Pharm. Pharmac., Aug. 1977, 29(8):500-501.
Consroe et al., "Anticonvulsant Nature of Marihuana Smoking," JAMA, Oct. 1975, 234(3):306-307.
Consroe et al., "Cannabidiol—Antiepileptic Drug Comparisons and Interactions in Experimentally Induced Seizures in Rats," J. Pharm. Exp. Therap., Apr. 1977 , 201(1):26-32.
Consroe et al., "Effects of Cannabidiol on Behavioral Seizures Caused by Convulsant Drugs or Current in Mice," Eur J Pharm, Sep. 1982, 83(3-4):293-298.
Consroe et al., "Chapter 2: Therapeutic Potential of Cannabinoids in Neurological Disorders," Cannabinoids as Therapeutic Agents, R. Mechoulam ed., 1986, 21-49.
Cortesi et al., "Potential therapeutical effects of cannabidiol in children with pharmacoresistant epilepsy," Med Hypotheses., 2007, 68(4):920-921.
Cortez and Snead, "Chapter 10: Pharmacologic Models of Generalized Absence Seizures in Rodents," Models of Seizures and Epilepsy, 2006, 111-126.
Crespel, et al., "Chapter 14: Lennox-Gastaut Syndrome," Epileptic Syndromes in Infancy, Childhood, and Adolescence, 2012, 5th Edition, ed. M. Bureau, 189-216.
Cunha et al., "Chronic Administration of Cannabidiol to Healthy Volunteers and Epileptic Patients," Pharmacology, 1980. 21(3):175-185.
Czapinski et al., "Mar. 17, 2008: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.
Dasa et al., "Key Attributes of TKDL: Ganja," Brhat Nighantu Ratnakara (Saligramanighantubhusanam), 1997, 6 pages (with English translation).

Davis and Ramsey, "Antiepileptic action of marihuana-active substances," Federation Proceedings., Mar. 1949, 8:284-285.
Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.
De Meijer, "Chapter 5: The Chemical Phenotypes (Chemotypes) of Cannabis," Handbook of Cannabis, ed. Roger G. Pertwee, 2014, 89-110.
De Oliveira, et al., "Anticonvulsant activity of β-caryophyllene against pentylenetetrazol-induced seizures," Epilepsy Behav, Mar. 2016, 56:26-31.
Deshpande et al., "Cannabinoid CBI Receptor Antagonists Cause Status Epilepticus-like Activity in the Hippocampal Neuronal Culture Model of Acquired Epilepsy," Neurosci Lett., Jan. 2007, 411: 11-16.
Devinsky et al., "Cannabidiol: Pharmacology and potential therapeutic role in epilepsy and other neuropsychiatric disorders," Epilepsia, 2014, 55(6):791-802.
Dravet, "The core Dravet syndrome phenotype," Epilepsia, Apr. 2011, 52(Suppl 2): 3-9.
Dreifus et al., "Proposal for Revised Clinical and Electroencephalographic Classification of Epileptic Seizures," Epilepsia, Aug. 1981, 22:489-501.
Dulac and Kaminska, "Use of Lamotrigine in Lennox-Gastaut and Related Epilepsy Syndromes," J. Child Neurolog., Nov. 1997, 12(S1): S23-S29.
Dulac et al., "Vigabatrin in Childhood Epilepsy," J. Child Neurolog., 1991, 6(S2): S30-S37.
Eadie, "Shortcomings in the current treatment of epilepsy," Expert Rev Neurother., Dec. 2012, 12(12): 1419-1427.
Eggers, "Temporal lobe epilepsy is a disease of faulty neuronal resonators rather than oscillators, and all seizures are provoked, usually by stress," Med Hypotheses, 2007, 69(6): 1284-1289.
ElSohly and Gul, "Chapter 1: Constituents of *Cannabis sativa*," Handbook of Cannabis, 2014, ed. Roger G. Pertwee, 3-22.
Engel et al., "Chapter 1: What Should be Modeled?," In Models Seizure Epilepsy., 2006, 14 pages.
Engel, "Report of the ILAE Classification Core Group," Epilepsia, 2006, 47(9):1558-1568.
EPO Annex to the Communication in Opposition for European Appln. No. 10734541.5, dated Jan. 28, 2016, 5 pages.
EPO Auxiliary Requests to the File in European Patent No. EP2448637, dated Nov. 2, 2016, 45 pages.
EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, Dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.

(56) References Cited

OTHER PUBLICATIONS

EPO Opposition, Expert Statement of Professor Anthony G Marson in European Appln. No. EP10734541.5, dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5, dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541.5, dated Dec. 5, 2014, 14 pages.
EPO Third Party Observations in European Appln. No. EP10734541.5, dated Apr. 3, 2017, 19 pages.
EPO Third Party Observations in European Appln. No. EP11712658.1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm>, 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Examination Report in GB Appln. No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufinamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.

(56) References Cited

OTHER PUBLICATIONS

GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic," Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*INSYS Development Company, Inc. v. GW Pharma Limited and Otsuka Pharmaceutical Co., Ltd.*, Decision in IPR2017-00503, U.S. Pat. No. 9,066,920, dated Jul. 7, 2017, 26 pages.
*INSYS Development Company, Inc. v. GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*INSYS Development Company, Inc. v. GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*INSYS Development Company, Inc. v. GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*INSYS Development Company, Inc. v. GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*INSYS Development Company, Inc. v. GW Pharma Limited and Otsuka Pharmaceutical Co., Ltd.*, Deposition of H. Steve White, dated Dec. 13, 2016, 50 pages.
*INSYS Development Company, Inc. v. GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*INSYS Development Company, Inc. v. GW Pharma Limited and Otsuka Pharmaceutical Co., Ltd.*, Petition for *Inter Partes* Review, IPR2017-00503, U.S. Pat. No. 9,066,920, dated Dec. 16, 2016, 78 pages.
*INSYS Development Company, Inc. v. GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*INSYS Development Company, Inc. v. GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
*INSYS Development Company, Inc. v. GW Pharma Limited and Otsuka Pharmaceutical Co., Ltd.*, Petitioner's Reply to Response in IPR2017-00503, U.S. Pat. No. 9,066,920, dated Jan. 19, 2018, 36 pages.
IUPHAR/BPS Guide to Pharmacology [online], "Entry for $\Delta$9-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.
Iuvone et al., "Neuroprotective Effect of Cannabidiol, a Non-psychoactive Component From *Cannabis sativa*, on $\beta$-amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol Use in Pediatric Treatment-Resistant Epilepsy", Apr. 2013, URL <https://www.theint.com/uploads/1/9/3/7/19371199/cannabidiol_use_in_pediatric_epilepsy.pdf>, 1 page.
Jeavons et al., "Sodium Calproate in Treatment of Epilepsy," Br Med J., Jun. 15, 1974, 2(5919): 584-586.
Jones et al. [online], Info & Metrics / Article Information,"Cannabidiol Displays Antiepileptiform and Antiseizure Properties in Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The Cannabinoids as Potential Antiepileptics," J Clin Pharmacol., Aug.-Sep. 1981, 21:437S-448S.
Kelley et al., "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Advia, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).
Klitgaard et al., "Electrophysiological, neurochemical and regional effects of levetiracetam in the rat pilocarpine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):191-206.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kwan et al., "Definition of drug resistant epilepsy: consensus proposal by the ad hoc Task Force of the ILAE Commission on Therapeutic Strategies," Epilepsia, Jun. 2010, 51(6):1069-1077.

(56) References Cited

OTHER PUBLICATIONS

LeafScience.com [online], "What are the Highest CBD Strains?" Oct. 15, 2014, retrieved on Feb. 16, 2017, URL <www.leafscience.com/2014/10/15/highest-cbd-strains/>, 2 pages.

Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.

Lieu et al., "Assessment of self-selection bias in a pediatric unilateral hearing loss study," Otolaryngol Head Neck Surg, Mar. 2010, 142(3): 427-433.

Lindamood and Colasanti, "Effects of $\Delta^9$-Tetrahydrocannabinol and Cannabidiol on Sodium-Dependent High Affinity Choline Uptake in the Rat Hippocampus1," J Pharmacology Experimental Therapeutics, 1980, 213(2):216-221.

Long et al., "The Pharmacological actions of cannabidiol," Drugs of the Future, Jul. 2005, 30(7): 747-753.

Löscher and Schmidt, "Modern antiepileptic drug development has failed to deliver: ways out of the current dilemma." Epilepsia, Apr. 2011, 52(4):657-78.

Lowenstein "Chapter 363: Seizures and Epilepsy," Diseases of the Central Nervous System, 2008, 2498-2512.

Luttjohann et al., "A Revised Racine's scale for PTZ-induced seizures in rats," Physiology & Behavior, 2009, 98:579-586.

Lutz, "On-demand activation of the endocannabinoid system in the control of neuronal excitability and epileptiform seizures," Biochemical Pharmacology, Nov. 2004, 68(9):1691-1698.

Maa et al., "The Case for Medical Marijuana in Epilepsy," Epilepsia, Jun. 2014, 55(6):783-786.

Mackie, "Cannabinoid Receptors as Therapeutic Targets," Annu Rev Pharmacol Toxicol, 2006, 46:101-122.

Majoosi et al., "Key Attributes of TKDL: Saoot Baraae Sara," Kaamil-al-Sena'ah, Central Council for Research in Unani Medicine, 2005, 2 pages (with English translation).

Malfait et al., "The nonpsychoactive cannabis constituent cannabidiol is an oral anti-arthritic therapeutic in murine collagen-induced arthritis," PNAS, Aug. 15, 2000, 97(17):9561-9566.

Manni et al., "Obstructive Sleep Apnea in a Clinical Series of Adult Epilepsy Patients: Frequency and Features of the Comorbidity," Epilepsia, Jun. 2003, 44(6): 836-840.

Manno, "Status Epilepticus: Current Treatment Strategies," The Neurohospitalist, Jan. 2011, 1(1):23-31.

Mares et al., "Chapter 12: Electrical Stimulation-Induced Models of Seizures," Models of Seizures and Epilepsy, Asla Pitkänen, Philip A. Schwartzkroin & Solomon L. Moshé, eds., 2004, 153-159.

Martin et al., "Structure-Anticonvulsant Activity Relationships of Cannabidiol Analogs," National Institute on Drug Abuse, Research Monograph Series, 1987, 79:48-58.

Mattson et al., "Comparison of carbamazepine, phenobarbital, phenytoin, and primidone in partial and secondarily generalized tonic-clonic seizures," N Engl J Med, Jul. 18, 1985, 313(3):145-151.

Mattson et al., "Prognosis for total control of complex partial and secondary generalized tonic clonic seizures," Neurology, 1996, 47:68-76.

McCormick et al., "On the Cellular Network Bases of Epileptic Seizures," Annu Rev Physiol, 2001, 63:815-846.

McNamara, "Chapter 19: Pharmacotherapy of the Epilepsies,", Goodman & Gilman's The Pharmacological Basis of Therapeutics 11th ed., McGraw-Hill Companies, 2006, 501-525.

Mechoulam et al., "Cannabidiol: An Overview of Some Pharmacological Aspects," J Clin Pharmacol, 2002, 42:11S-19S.

Mechoulam et al., "Toward drugs derived from cannabis," Naturwissenschaften, Apr. 1978, 65(4): 174-179.

Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.

Merlis, "Proposal for an International Classification of the Epilepsies," Epilepsia, 1970, 11:114-119.

Miller et al., "Mapping genetic modifiers of survival in a mouse model of Dravet syndrome," Genes, Brain and Behavior, 2014, 13:163-172.

Moral et al., "Pipeline on the Move," Drugs of the Future, Jan. 2014, 39(1): 49-56.

Morard et al., "Conversion to Sirolimus-Based Immunosuppression in Maintenance Liver Transplantation Patients," Liver Transplantation, 2007, 13:658-664.

Neto et al., "The role of polar phytocomplexes on anticonvulsant effects of leaf extracts of Lippia Alba (Mill.) N.E. Brown chemotypes," J. Pharm Pharmacol, 2009, 61(7):933-939.

Ng et al., "Illicit Drug Use and the Risk of New-Onset Seizures," Am J Epidemiol, 1990, 132(1):47-57.

Oakley et al., "Dravet Syndrome Insights into pathophysiology and therapy from a mouse model of Dravet syndrome," Epilepsia, Apr. 2011, 52(Suppl. 2): 59-61.

Obay et al., "Antiepileptic effects of ghrelin on pentylenetetrazole-induced seizures in rats," Peptides, Jun. 2007, 28(6):1214-1219.

PCT International Preliminary Report on Patentability in International Appln. No. PCT/GB2010/051066, dated Jun. 9, 2011, 6 pages.

PCT International Preliminary Report on Patentability in International Appln. No. PCT/GB2012/052284, dated Dec. 12, 2013, 12 pages.

PCT International Preliminary Report on Patentability in International Appln. No. PCT/GB2015/051775, dated Aug. 10, 2016, 9 pages.

PCT International Preliminary Report on Patentability in International Appln. No. PCT/GB2015/053030, dated Apr. 18, 2017, 6 pages.

PCT International Preliminary Report on Patentability in International Appln. No. PCT/GB2016/051792, dated Sep. 1, 2017, 14 pages.

PCT International Search Report and Written Opinion in International Appln. No. PCT/GB2010/051066 dated Dec. 13, 2010, 8 pages.

PCT International Search Report and Written Opinion in International Appln. No. PCT/GB2011/050649, dated May 30, 2011, 15 pages.

PCT International Search Report and Written Opinion in International Appln. No. PCT/GB2012/052284, dated Nov. 16, 2012, 11 pages.

PCT International Search Report and Written Opinion in International Appln. No. PCT/GB2015/051775, dated Aug. 26, 2015, 11 pages.

PCT International Search Report and Written Opinion in International Appln. No. PCT/GB2015/051776, dated Aug. 25, 2015, 11 pages.

PCT International Search Report and Written Opinion in International Appln. No. PCT/GB2016/052340, dated Oct. 25, 2016, 12 pages.

PCT International Search Report and Written Opinion in International Appln. PCT/GB2017/051943, dated Sep. 12, 2017, 10 pages.

PCT International Search Report in International Appln. No. PCT/GB2012/050002, dated Feb. 24, 2012, 3 pages.

Pelliccia et al. [online], "Treatment with CBD in oily solution of drug-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.

Pereira et al., "Study pharmacologic of the GABAergic and glutamatergic drugs on seizures and status epilepticus induced by pilocarpine in adult Wistar rats," Neurosci Lett, Jun. 2007, 419(3): 253-257.

Pertwee, "Cannabinoid receptor ligands: clinical and neuropharmacological considerations, relevant to future drug discovery and development," Expert Opin Investig Drugs, Jul. 2000, 9(7): 1553-1571.

Pertwee, "Chapter 3: The Pharmacology and Therapeutic Potential of Cannabidiol," Cannabinoids, Ed Vincenzo Di Marzo ed., 2004, 32-83.

(56) References Cited

OTHER PUBLICATIONS

Pertwee, "The diverse CB1 and CB2 receptor pharmacology of three plant cannabinoids: Δ9-tetrahydrocannabinol, cannabidiol and Δ9-tetrahydrocannabivarin," Br. J. Pharmacol, 2008, 153(2):199-215.
Petrocellis et al., "Effects of cannabinoids and cannabinoid-enriched Cannabis extracts on TRP channels and endocannabinoid metabolic enzymes," British Journal of Pharmacology, 2011, 163: 1479-1494.
Pohl et al., "Effects of flunarizine on Metrazol-induced seizures in developing rats," Epilepsy Res, 1987, 1:302-305.
Poortman-van der Meer, "A contribution to the improvement of accuracy in the quantitation of THC," Forensic Science International, Apr. 1999, 101(1): 1-8.
Porter et al., "Randomized, multicenter, dose-ranging trial of retigabine for partial-onset seizures," Neurology, Apr. 2007, 68(15): 1197-1204.
Porter et al., "Report of a Parent Survey of Cannabidiol-enriched Cannabis use in Pediatric Treatment-resistant Epilepsy," Epilepsy Behavior, Dec. 2013, 29(3): 574-577.
Potter, "Chapter 4: Cannabis Horticulture," Handbook of Cannabis, ed. Roger G. Pertwee, 2014, 65-88.
Pouton, "Lipid formulations for oral administration of drugs: non-emulsifying, self-emulsifying and 'self-microemulsifying' drug delivery systems," Eur. J Pharm Sci, Oct. 2000, 11(Supp. 2): S93-S98.
Press et al., "Parental reporting of response to oral cannabis extracts for treatment of refractory epilepsy," Epilepsy Behav, Apr. 2015, 45:49-52.
Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.
Ramantani et al., "Epilepsy in Aicardi—Goutieres syndrome," Official J Eur Paediatric Neurology Society, 2014, 18: 30-37.
Rauca et al., "The role of superoxide dismutase and a-tocopherol in the development of seizures and kindling induced by pentylenetetrazol—influence of the radical scavenger a-phenyl-N-tert-butyl nitron," Brain Research, May 29, 2004 , 1009(1-2):203-212.
Resstel et al., "5-$HT_{1A}$ receptors are involved in the cannabidiol-induced attenuation of behavioural and cardiovascular responses to acute restraint stress in rats," Br J Pharmacol, Jan. 2009, 156(1): 181-188.
Rosenberg et al., "Cannabinoids and Epilepsy," Neurotherapeutics, Oct. 2015, 12(4): 747-768.
Rubio et al., "In Vivo Experimental Models of Epilepsy," Central Nervous System Agents in Medicinal Chemistry, 2010, 10:298-309.
Russo, "Taming THC: potential cannabis synergy and phytocannabinoid-terpenoid entourage effects," British J. of Pharm, 2011, 163:1344-1364.
Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phyther Res, May 2009, 23(5):597-602.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.

Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 2004, 140:83-93.
Swann., "The Effects of Seizures on the Connectivity and Circuitry of the Developing Brain," MRDD, 2004, 10(2):96-100.
Thomas et al., "Evidence that the Plant Cannabinoid Δ9-Tetrahydrocannabivarin is a Cannabinoid CBI and CB2 Receptor antagonist," Br J Pharmacol, Dec. 2005, 146(7):917-926.
Thumma et al., "Influence of plasticizers on the stability and release of a prodrug of Δ9-tetrahydrocannabinol incorporated in poly(ethylene oxide) matrices," Eur J Pharmceutics and Biopharmaceutics, Oct. 2008, 70(2): 605-614.
Thurman et al., "Standards for epidemiologic studies and surveillance of epilepsy," Epilepsia, Sep. 2011, 52 Suppl 7: 2-26.
Thurstone, "Avoid Charlotte's Web for Epilepsy," Jun. 26, 2014, URL <http://drthurstone.com/charlotted-web-not-safest-option-epiliepsy-treatment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
Unimed Pharmaceuticals, Inc., "Marinol®," Jul. 2006 <https://www.accessdata.fda.gov/drugsatfda_docs/label/2006/018651s025s0261b1.pdf>, 11 pages.
Usami et al., "Synthesis and Pharmacological Evaluation in Mice of Halogenated Cannabidiol Derivatives," Chem Pharm Bull, Nov. 1999, 47(11):1641-1645.
USPTO Decision on Appeal in U.S. Appl. No. 10/318,659 (Appeal 2009-011751), dated Jul. 8, 2010, 23 pages.
USPTO Decision on Appeal in U.S. Appl. No. 13/698,730 (Appeal 2016-006358), dated Jun. 21, 2017, 6 pages.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, Dec. 2008, 4(6): 1001-1019.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vollner et al., "Haschisch XX+ [Haschiscc XX+]: Cannabidivarin, a new hashish substance," Tetrahedron Letters, 1969, 10(3):145-147.
Wahle et al., "Development of Tolerance to the Anticonvulsant Effect of Valproate but not to Ethosuximide in a Rat Model of Absence Epilepsy," Eur J Pharma, May 1990, 181(1-2): 1-8.
Wallace et al., "Assessment of the role of CB1 receptors in cannabinoid anticonvulsant effects," European J Pharmacology, 2001, 428(1):51-57.
Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model of Epileptiform Activity," Proceedings of the British Pharm Society, Dec. 2006,

(56) References Cited

OTHER PUBLICATIONS retrieved on Mar. 1, 2017, URL <http://www.pA2online.org/abstract/abstract.jsp?abid=28533>, 1 page, Abstract Only.

Wikipedia.org [online], "Cannabinoid," Wikipedia, Apr. 2003, retrieved on Mar. 1, 2017, URL <https://en.wikipedia.org/wiki/Cannabinoid>, 15 pages.

Wingerchuk, "Cannabis for medical purposes: cultivating science, weeding out the fiction," Lancent, Jul. 2004, 364:315-316.

Yu et al., "Reduced sodium current in GABAergic interneurons in a mouse model of severe myoclonic epilepsy in infancy," Nature Neuroscience, Sep. 2006, 9(9): 1142-1149.

Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).

Zhao et al., "Chapter 27: Repetitive Seizures in the Immature Brain," Models of Seizures and Epilepsy, 2006, 341-350.

Zhornitsky and Potvin, "Cannabidiol in Humans—The Quest for Therapeutic Targets," Pharmaceuticals, 2012, 5:529-552.

Zuardi et al., "Cannabidiol, a Cannabis sativa constituent, as an antipsychotic drug," Brazilian Journal of Medicine and Biological Research, Apr. 2006, 39(4): 421-429.

Zuardi et al., "Cannabidiol: from an inactive cannabinoid to a drug with wide spectrum of action," Rev Bras Psiquiatr, 2008, 30(3): 271-80.

[No Author Listed], "Missouri House passes cannabis extract legislation," Kansas City Star, 2014, https://kansascity.com/news/politics-government/article346747.html, 2 pages.

Banerjee et al., "Case Report: Aicardi syndrome: A report of five Indian cases," Neurology India, Mar. 2006, 54(1): 91-93.

Chou, "Theoretical basis, experimental design, and computerized simulation of synergism and antagonism in drug combination studies," Pharmacol Rev., Sep. 2006, 58(3), 621-681.

GB Combined Search and Examination Report in GB Appln. No. GB1605448.8, dated Jan. 12, 2017, 6 pages.

*INSYS Development Company, Inc.* v. *GW Pharma Limiied and Otsuka Pharmaceutical Co., Ltd.*, Final Written Decision in IPR2017-00503, U.S. Pat. No. 9,066,920, dated Jan. 3, 2019, 40 pages.

Kuhn et al., "Potent activity of carfilzomib, a novel, irreversible inhibitor of the ubiquitin-proteasome pathway, against preclinical models of multiple myeloma," Blood, Nov. 2007, 110(9): 3281-3290.

Leo et al., "Cannabidiol and epilepsy: Rationale and therapeutic potential," Pharamacological Research, Mar. 2016, 107: 85-92.

Morelli et al., "The effects of cannabidiol and its synergism with bortezomib in multiple myeloma cell lines. A role for transient receptor potential Vanilloid type-2," Int J Cancer, Jun. 2014, 134(11): 2534-2546.

MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.

Nabissi et al, "Cannabinoids synergize with cafilzomib, reducing multiple myeloma cells viability and migration," Oncotarget, Oct. 2016, 7: 77553.

PCT International Preliminary Report on Patentability in International Appln. No. PCT/GB2017/052229, dated Feb. 26, 2019, 7 pages.

PCT International Preliminary Report on Patentability in International Appln. No. PCT/US2017/050868, dated Oct. 11, 2018, 7 pages.

PCT International Search Report and Written Opinion in International Appln. No. PCT/GB2017/051913, dated Sep. 15, 2017, 9 pages.

PCT International Search Report and Written Opinion in International Appln. No. PCT/GB2017/051914, dated Sep. 12, 2017, 10 pages.

PCT International Search Report and Written Opinion in International Appln. No. PCT/GB2017/052229, dated Oct. 6, 2017, 10 pages.

PCT International Search Report and Written Opinion in International Appln. No. PCT/US2017/050868, dated Aug. 6, 2017, 14 pages.

Pruitt et al., "Ethanol in Liquid Preparations Intended for Children," Padiatrics, Mar. 1984: 73(3): 405-407.

Raab et al., "Multiple myeloma," Lancet, Jul. 2009, 374(9686): 324-339.

Rosenkntz et al., "Oral and Parenteral Formulations of Marijuana Constituents," J Pharm Sci, Jul. 1972, 61(7)1106-1112.

Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.

Strickley, "Solubilizing Excipients in Oral and Injectable Formulations," Table VIII, Pharmaceutical Research, Feb. 2004, 21(2): 201-230.

Velasco et al., "Anticancer mechanisms of cannabinoids," Curr Oncol, Mar. 2016, 23(2): S23-S32.

\* cited by examiner

USE OF CANNABINOIDS IN THE TREATMENT OF EPILEPSY

This application is a National Stage application under 35 U.S.C. § 371 of International Application No. PCT/GB2016/052340, having an International Filing Date of Jul. 29, 2016, which claims the benefit of GB Serial No. 1514079.1 filed Aug. 10, 2015. This disclosure of the prior applications are considered part of (and are incorporated by reference in) the disclosure of this application.

FIELD OF THE INVENTION

The present invention relates to the use of a therapeutically effective amount of cannabidiolic acid (CBDA) in the treatment of epilepsy. In one embodiment the CBDA is used in the treatment of generalised seizures, preferably tonic-clonic seizures.

Preferably the CBDA used is in the form of a botanical drug substance in which the CBDA content is greater than 60%, and most preferably, it is a highly purified extract of *cannabis* such that the CBDA is present at greater than 95%, through 96% and 97% to most preferably, greater than 98% of the total extract (w/w) and the other components of the extract are characterised. In particular the cannabinoids tetrahydrocannabinol (THC) or tetrahydrocannabinol acid (THCA) have been substantially removed. Alternatively, the CBDA may be synthetically produced.

In use the CBDA may be used concomitantly with one or more other anti-epileptic drugs (AED). Alternatively the CBDA may be formulated for administration separately, sequentially or simultaneously with one or more AED or the combination may be provided in a single dosage form. Where the CBDA is formulated for administration separately, sequentially or simultaneously it may be provided as a kit or together with instructions to administer the one or more components in the manner indicated. It may also be used as the sole medication, i.e. as a monotherapy.

BACKGROUND TO THE INVENTION

Epilepsy occurs in approximately 1% of the population worldwide, (Thurman et al., 2011) of which 70% are able to adequately control their symptoms with the available existing anti-epileptic drugs (AED). However, 30% of this patient group, (Eadie et al., 2012), are unable to obtain seizure freedom using the AED that are available and as such are termed as suffering from intractable or "treatment-resistant epilepsy" (TRE).

Intractable or treatment-resistant epilepsy was defined in 2009 by the International League Against Epilepsy (ILAE) as "failure of adequate trials of two tolerated and appropriately chosen and used AED schedules (whether as monotherapies or in combination) to achieve sustained seizure freedom" (Kwan et al., 2009).

Individuals who develop epilepsy during the first few years of life are often difficult to treat and as such are often termed treatment-resistant. Children who undergo frequent seizures in childhood are often left with neurological damage which can cause cognitive, behavioral and motor delays.

Childhood epilepsy is a relatively common neurological disorder in children and young adults with a prevalence of approximately 700 per 100,000. This is twice the number of epileptic adults per population.

When a child or young adult presents with a seizure, investigations are normally undertaken in order to investigate the cause. Childhood epilepsy can be caused by many different syndromes and genetic mutations and as such diagnosis for these children may take some time.

The main symptom of epilepsy is repeated seizures. In order to determine the type of epilepsy or the epileptic syndrome that a patient is suffering from, an investigation into the type of seizures that the patient is experiencing is undertaken. Clinical observations and electroencephalography (EEG) tests are conducted and the type(s) of seizures are classified according to the ILAE classification described below and in FIG. 1.

The International classification of seizure types proposed by the ILAE was adopted in 1981 and a revised proposal was published by the ILAE in 2010 and has not yet superseded the 1981 classification. FIG. 1 is adapted from the 2010 proposal for revised terminology and includes the proposed changes to replace the terminology of "partial" with "focal". In addition the term "simple partial seizure" has been replaced by the term "focal seizure where awareness/responsiveness are not impaired" and the term "complex partial seizure" has been replaced by the term "focal seizure where awareness/consciousness are impaired".

From FIG. 1 it can be seen that Generalised seizures, where the seizure arises within and rapidly engages bilaterally distributed networks, can be split into six subtypes: Tonic-Clonic (grand mal) seizures; Absence (petit mal) Seizures; Clonic Seizures; Tonic Seizures; Atonic Seizures and Myoclonic Seizures.

Focal (partial) seizures where the seizure originates within networks limited to only one hemisphere, are also split into sub-categories. Here the seizure is characterized according to one or more features of the seizure, including aura, motor, autonomic and awareness/responsiveness. Where a seizure begins as a localized seizure and rapidly evolves to be distributed within bilateral networks this seizure is known as a Bilateral convulsive seizure, which is the proposed terminology to replace Secondary Generalized Seizures (generalized seizures that have evolved from focal seizures and no longer remain localized).

Focal seizures where the subject's awareness/responsiveness is altered are referred to as focal seizures with impairment and focal seizures where the awareness or responsiveness of the subject is not impaired are referred to as focal seizures without impairment.

Focal seizures may occur in epilepsy syndromes including: Lennox-Gastaut Syndrome; Tuberous Sclerosis Complex; Dravet Syndrome; CDKL5; Neuronal ceroid lipofuscinoses (NCL); febrile infection related epilepsy syndrome (FIRES); Aicardi syndrome and brain abnormalities.

Epileptic syndromes often present with many different types of seizure and identifying the types of seizure that a patient is suffering from is important as many of the standard AED are targeted to treat or are only effective against a given seizure type/sub-type.

Common AED defined by their mechanisms of action are described in the following tables:

TABLE 1

Examples of narrow spectrum AED

| Narrow-spectrum AED | Mechanism | Indication |
|---|---|---|
| Phenytoin | Sodium channel | Complex partial Tonic-clonic |
| Phenobarbital | GABA/Calcium channel | Partial seizures Tonic-clonic |

TABLE 1-continued

Examples of narrow spectrum AED

| Narrow-spectrum AED | Mechanism | Indication |
| --- | --- | --- |
| Carbamazepine | Sodium channel | Partial seizures<br>Tonic-clonic<br>Mixed seizures |
| Oxcarbazepine | Sodium channel | Partial seizures<br>Tonic-clonic<br>Mixed seizures |
| Gabapentin | Calcium channel | Partial seizures<br>Mixed seizures |
| Pregabalin | Calcium channel | Adjunct therapy for partial seizures with or without secondary generalisation |
| Lacosamide | Sodium channel | Adjunct therapy for partial seizures |
| Vigabatrin | GABA | Secondarily generalized tonic-clonic seizures<br>Partial seizures<br>Infantile spasms due to West syndrome |

TABLE 2

Examples of broad spectrum AED

| Broad-spectrum AED | Mechanism | Indication |
| --- | --- | --- |
| Valproic acid | GABA/Sodium channel | First-line treatment for tonic-clonic seizures, absence seizures and myoclonic seizures<br>Second-line treatment for partial seizures and infantile spasms.<br>Intravenous use in status epilepticus |
| Lamotrigine | Sodium channel | Partial seizures<br>Tonic-clonic<br>Seizures associated with Lennox-Gastaut syndrome |
| Ethosuximide | Calcium channel | Absence seizures |
| Topiramate | GABA/Sodium channel | Seizures associated with Lennox-Gastaut syndrome |
| Zonisamide | GABA/Calcium/Sodium channel | Adjunctive therapy in adults with partial-onset seizures<br>Infantile spasm<br>Mixed seizure<br>Lennox-Gastaut syndrome<br>Myoclonic<br>Generalised tonic-clonic seizure |
| Levetiracetam | Calcium channel | Partial seizures<br>Adjunctive therapy for partial, myoclonic and tonic-clonic seizures |
| Clonazepam | GABA | Typical and atypical absences<br>Infantile myoclonic<br>Myoclonic seizures<br>Akinetic seizures |
| Rufinamide | Sodium channel | Adjunctive treatment of partial seizures associated with Lennox-Gastaut syndrome |

TABLE 3

Examples of AED used specifically in childhood epilepsy

| AED | Mechanism | Indication |
| --- | --- | --- |
| Clobazam | GABA | Adjunctive therapy in complex partial seizures<br>Status epilepticus<br>Myoclonic<br>Myoclonic-absent |
| Stiripentol | GABA | Simple partial<br>Complex partial<br>Absence seizures<br>Lennox-Gastaut syndrome<br>Severe myoclonic epilepsy in infancy (Dravet syndrome) |

Over the past forty years there have been a number of animal studies on the use of the non-psychoactive cannabinoid cannabidiol (CBD) to treat seizures. For example, Consroe et al., (1982) determined that CBD was able to prevent seizures in mice after administration of pro-convulsant drugs or an electric current.

Studies in epileptic adults have also occurred in the past forty years with CBD. Cunha et al. reported that administration of CBD to eight adult patients with generalized epilepsy resulted in a marked reduction of seizures in 4 of the patients (Cunha et al., 1980).

A study in 1978 provided 200 mg/day of pure CBD to four adult patients, two of the four patients became seizure free, whereas in the remainder seizure frequency was unchanged (Mechoulam and Carlini, 1978).

In contrast to the studies described above, an open label study reported that 200 mg/day of pure CBD was ineffective in controlling seizures in twelve institutionalized adult patients (Ames and Cridland, 1986).

Based on the fact that chronologically the last study to look at the effectiveness of CBD in patients with epilepsy suggested that CBD was unable to control seizures, there may be less of an expectation that CBD might be useful as an anti-convulsant agent.

In the past forty years of research there have been over thirty drugs approved for the treatment of epilepsy none of which are cannabinoids. Indeed, there appears to have been a prejudice against cannabinoids, possibly due to the scheduled nature of these compounds and/or the fact that THC, which is a known psychoactive, has been ascribed as a pro-convulsant (Consroe et al., 1977).

A paper published recently suggested that cannabidiol-enriched *cannabis* may be efficacious in the treatment of epilepsy. Porter and Jacobson (2013) report on a parent survey conducted via a Facebook group which explored the use of *cannabis* which was enriched with CBD in children with treatment-resistant epilepsy. It was found that sixteen of the 19 parents surveyed reported an improvement in their child's epilepsy. The children surveyed for this paper were all taking *cannabis* extracts that were purported to contain CBD in a high concentration although the amount of CBD present and the other constituents including THC and non-cannabinoid components such as terpenes were not known for many of the cases. Indeed, whilst CBD levels ranged from 0.5 to 28.6 mg/kg/day (in those extracts tested), THC levels as high as 0.8 mg/kg/day were reported.

Providing children with TRE with a *cannabis* extract that comprises THC, which has been described as a pro-convulsant (Consroe et al., 1977), at a potentially psychoactive dose of 0.8 mg/kg/day is not desirable.

Whilst decoctions of *cannabis* which will contain CBDA as well as THCA along with other cannabinoids and non-cannabinoid components have been used in epilepsy, treatments have not focussed on isolated or highly purified CBDA. Rather the recent focus has been on the use of the decarboxylated form of CBDA, CBD in the treatment of epilepsy.

CBDA has however been found to be effective in the treatment of nausea as is shown in WO 2003/063847 and as a TNF alpha inhibitor suggested for use in treating immunomodulatory and anti-inflammatory conditions as is shown in WO 2002/064109.

The patent application GB 2,495,118 describes the use of a composition comprising CBDV and CBD for use in the treatment of epilepsy. Furthermore the application WO 2011/121351 describes the use of CBDV in the treatment of epilepsy. Both documents describe the use of a CBDV botanical drug substance which comprises a small quantity of undecarboxylated CBD as CBDA. The CBDA is present in very small amounts and as such is not present in therapeutically effective amounts.

The patent application US 2015/126595 describes the use of a transdermal composition comprising cannabinoids including CBDA.

Patent applications CA 2,859,934 and CA 2,737,447 both describe a medicinal *cannabis* chemovar which comprises the compound CBDA. It is readily understood that all *cannabis* plants produce cannabinoids in their acid form which are then readily decarboxylated to produce the traditionally recognised active form CBD.

Whilst CBD now appears to be a promising candidate as an anti-epileptic drug there are a number of potential limitations including: the relative large doses that appear necessary; and CBD's relatively poor bioavailability.

Therefore it is desirable to find other compounds which may demonstrate activity and/or specificity to particular seizure sub-types and which might be administered in lower concentrations. This has the benefit of smaller administration forms and with improved bioavailability lower dose may be required and onset to action may be quicker.

BRIEF SUMMARY OF THE DISCLOSURE

In accordance with a first aspect of the present invention there is provided a therapeutically effective amount of cannabidiolic acid (CBDA) for use in the treatment of epilepsy.

In one embodiment the epilepsy is generalised epilepsy. More preferably the epilepsy is characterized by tonic-clonic seizures.

A therapeutically effective amount is preferably at least 0.1 mg, preferably at least 0.5 mg, more preferably at least 1 mg, more preferably still at least 20 mg or more.

The CBDA used may be in the form of a botanical drug substance in which the CBDA content is greater than 60%, and most preferably, it is a highly purified extract of *cannabis* such that the CBDA is present at greater than 95%, through 96% and 97% to most preferably, greater than 98% of the total extract (w/w) and the other components of the extract are characterised. In particular the cannabinoids tetrahydrocannabinol (THC) or tetrahydrocannabinol acid (THCA) have been substantially removed. Preferably the highly purified extract comprises less than 1% (w/w) tetrahydrocannabinol (THC) or tetrahydrocannabinol acid (THCA).

Alternatively, the CBDA may be synthetically produced.

The CBDA may also be used concomitantly with one or more other cannabinoids. Preferably the CBDA is used with CBD.

Where CBDA is used in combination with CBD ratios of between 9:1 to 1:9 (CBDA:CBD) are preferred. Ranges of ratios include 8:2 to 2:8 (CBDA:CBD); 7:3 to 3:7 (CBDA:CBD); 6:4 to 4:6 (CBDA:CBD); and 1:1 (CBDA:CBD) and any ranges there between.

In a further embodiment of the invention the CBDA is used concomitantly with one or more other anti-epileptic drugs (AED).

The CBDA may be used at a daily dose of less than 1000 mg. Preferably, the daily dose of CBDA is less than 800 mg, preferably less than 600 mg, and more preferably less than 400 mg.

The daily dose may be less than 200 mg, less than 100 mg and as little as 10 mg or 1 mg may be used.

As the cannabinoid CBDA is more bioavailable than its neutral form CBD, it is likely that a far lower dose of CBDA will be required in comparison with CBD when treating the same indication. For example providing a human with a dose of 20 mg/kg of CBD to treat epilepsy may be effective, whereas the dose of CBDA required may be a log fold lower. Clearly such lower doses have benefits in treatment.

Furthermore the greater bioavailability of CBDA may mean that it can act more quickly than CBD. In other words the cannabinoid CBDA may have a lower $T_{max}$ than CBD. This quality could lead to useful combination products which comprise CBDA in combination with CBD. The CBDA may be useful in providing a rapid onset effect whereas the CBD may be useful in providing a sustained effect.

Ratioed amounts of CBDA to CBD, where the CBDA is the predominant cannabinoid are envisaged these include ranges from 95:5 to 55:45 (CBDA:CBD).

Alternatively the CBDA and CBD may be present in substantially equal amount namely 55:45 to 45:55 (CBDA:CBD). In yet a further embodiment the CBD may be the predominant cannabinoid and the range may be from 45:55 to 20:80 (CBDA:CBD).

Furthermore the faster acting CBDA may be a useful candidate for use in the treatment of epilepsy which requires immediate emergency treatment such as acute seizures or status epilepticus. Preferably the CBDA is administered via the parenteral route, for example by injection into the vein or the muscle.

In accordance with a second aspect of the present invention there is provided a method of treating epilepsy comprising administering a therapeutically effective amount of cannabidiolic acid (CBDA) to a subject.

Preferably the subject is a human.

In accordance with a third aspect of the present invention there is provided a composition for use in the treatment of epilepsy comprising a therapeutically effective amount of cannabidiolic acid (CBDA), and one or more pharmaceutically acceptable excipients.

It is envisaged that the composition be administered as one or more of: an oral liquid solution, solid, semi-solid, gel, injection, spray, aerosol, inhaler, vaporiser, enema or suppository. Such medicaments could be administered via the oral, buccal, sublingual, parenteral, respiratory, nasal and distal rectum route.

DEFINITIONS

Definitions of some of the terms used to describe the invention are detailed below:

The cannabinoids described in the present application are listed below along with their standard abbreviations.

TABLE 4

Cannabinoids and their abbreviations

| | | |
|---|---|---|
| CBD | Cannabidiol | 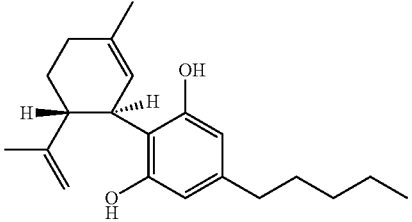 [SMILES: C=C(C)[C@@H]1CCC(C)=C[C@H]1c1c(O)cc(CCCCC)cc1O] |
| CBDA | Cannabidiolic acid | 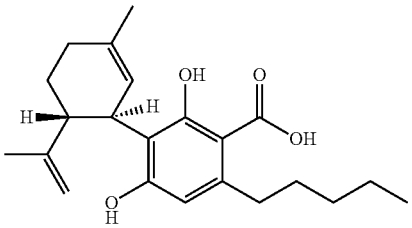 [SMILES: C=C(C)[C@@H]1CCC(C)=C[C@H]1c1c(O)cc(CCCCC)c(C(=O)O)c1O] |
| THC | Tetrahydrocannabinol | 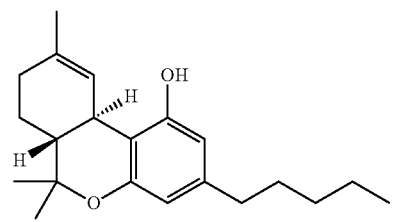 [SMILES: CCCCCc1cc(O)c2c(c1)OC(C)(C)[C@@H]1CCC(C)=C[C@@H]21] |
| THCA | Tetrahydrocannabinolic acid | 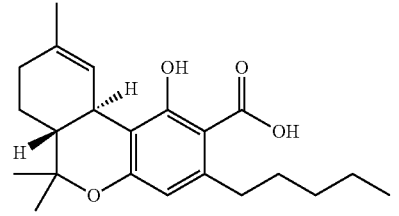 [SMILES: CCCCCc1cc2c(c(O)c1C(=O)O)[C@@H]1C=C(C)CC[C@H]1C(C)(C)O2] |

The table above is not exhaustive and merely details the cannabinoids which are identified in the present application for reference. So far over 60 different cannabinoids have been identified and these cannabinoids can be split into different groups as follows: Phytocannabinoids; Endocannabinoids and Synthetic cannabinoids (which may be novel cannabinoids or synthetically produced phytocannabinoids or endocannabinoids).

Patent application number WO 2004/026857 describes the analysis of highly purified CBDA. The CBDA is described as being purified to be greater than 98% pure, with less than 0.1% CBD, 0.3% THCA, and less than 0.1% THC.

"Phytocannabinoids" are cannabinoids that originate from nature and can be found in the *cannabis* plant. The phytocannabinoids can be isolated from plants to produce a highly purified extract or can be reproduced synthetically.

"Highly purified cannabinoid extracts" are defined as cannabinoids that have been extracted from the *cannabis* plant and purified to the extent that other cannabinoids and non-cannabinoid components that are co-extracted with the cannabinoids have been substantially removed, such that the highly purified cannabinoid is greater than or equal to 98% (w/w) pure.

"Synthetic cannabinoids" are compounds that have a cannabinoid or cannabinoid-like structure and are manufactured using chemical means rather than by the plant.

BRIEF DESCRIPTION OF THE DRAWINGS

Embodiments of the invention are further described hereinafter with reference to the accompanying drawings, in which.

LEGENDS TO THE FIGURES

Figure 1:
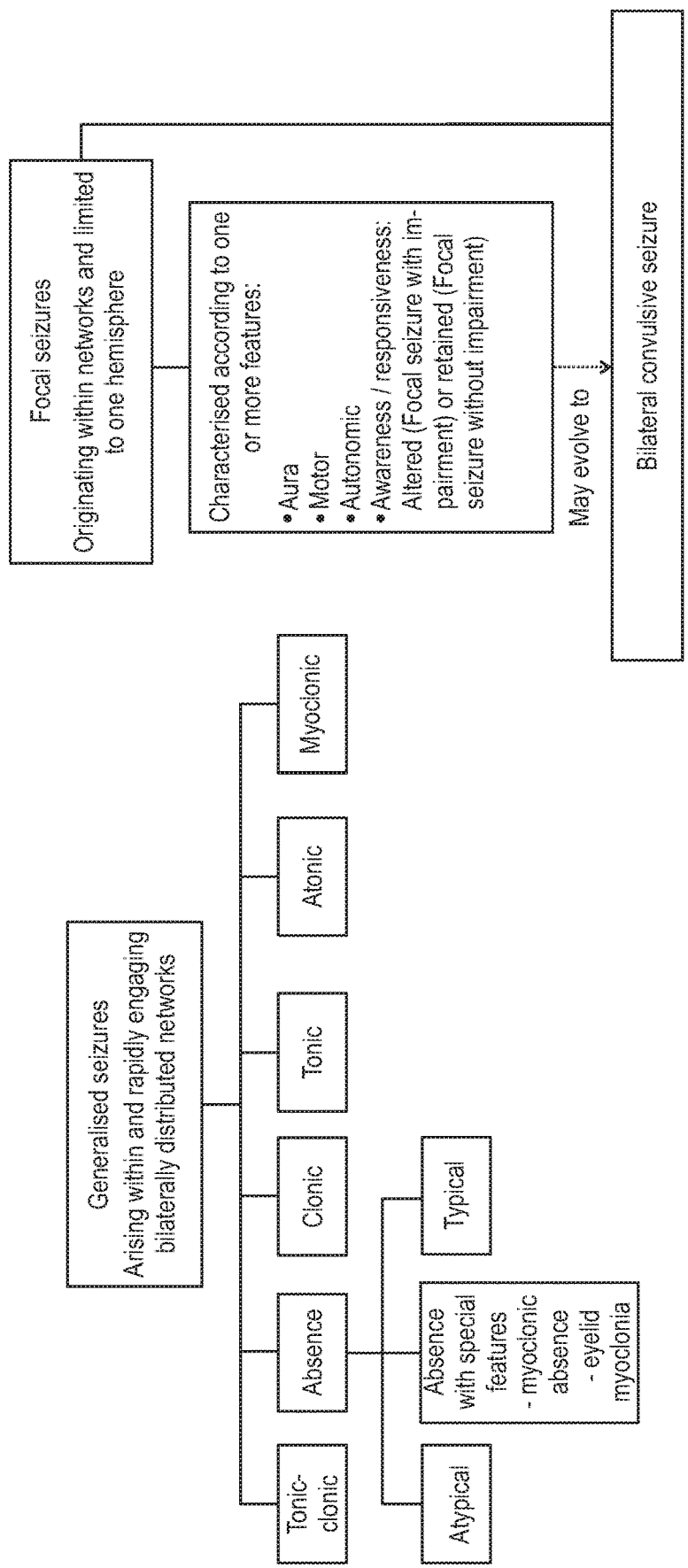
FIG. 1 shows the ILAE Proposal for Revised Terminology for Organisation of Seizures and Epilepsies 2010.
Figure 2:
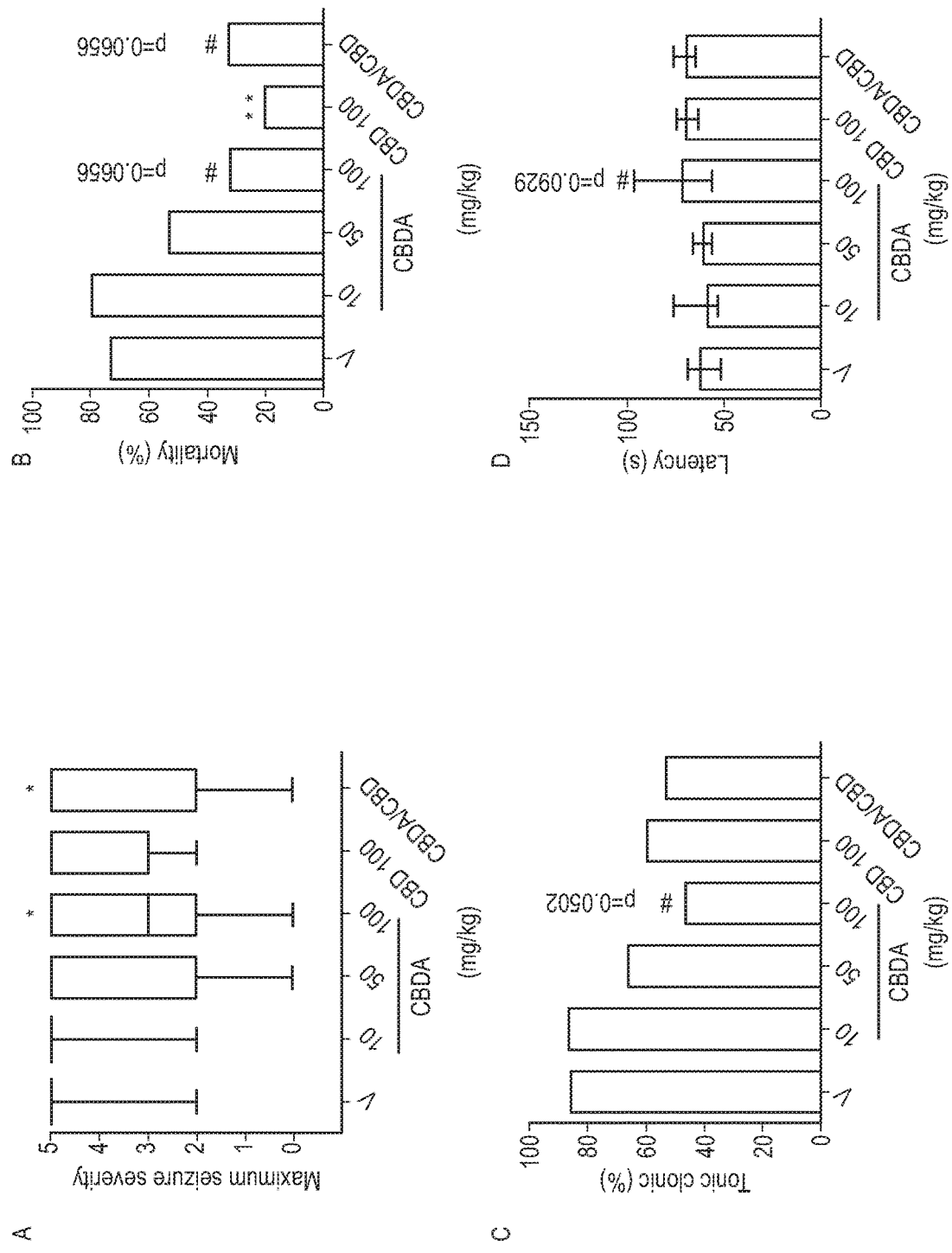
FIGS. 2 A, B, C and D show the effect of cannabinoids on PTZ-induced generalised seizures.

FIG. 2: Panels A-D illustrate the effect of CBDA (10-100 mg/kg), CBD (100 mg/kg), and CBD+CBDA (9:1 ratio) on seizure severity (A), percentage mortality (B), percentage of animals exhibiting tonic-clonic seizures (C) and latency to seizure onset (D). In panel A, median seizure severity is represented by a thick grey horizontal line, 25th and 75th percentiles by the black box and whiskers indicate the minimum and maximum values. In panel D, onset latency is presented as median with IQR. Statistical testing was performed using either a Kruskal-Wallis with post-hoc Mann-Whitney U-tests (panel A and D) or Chi-squared with post-hoc Fisher exact tests (panel B and C): P≤0.1 (#); P≤0.05 (*); P≤0.01 (); P≤0.001 (*); n=15 per group.

Figure 3:
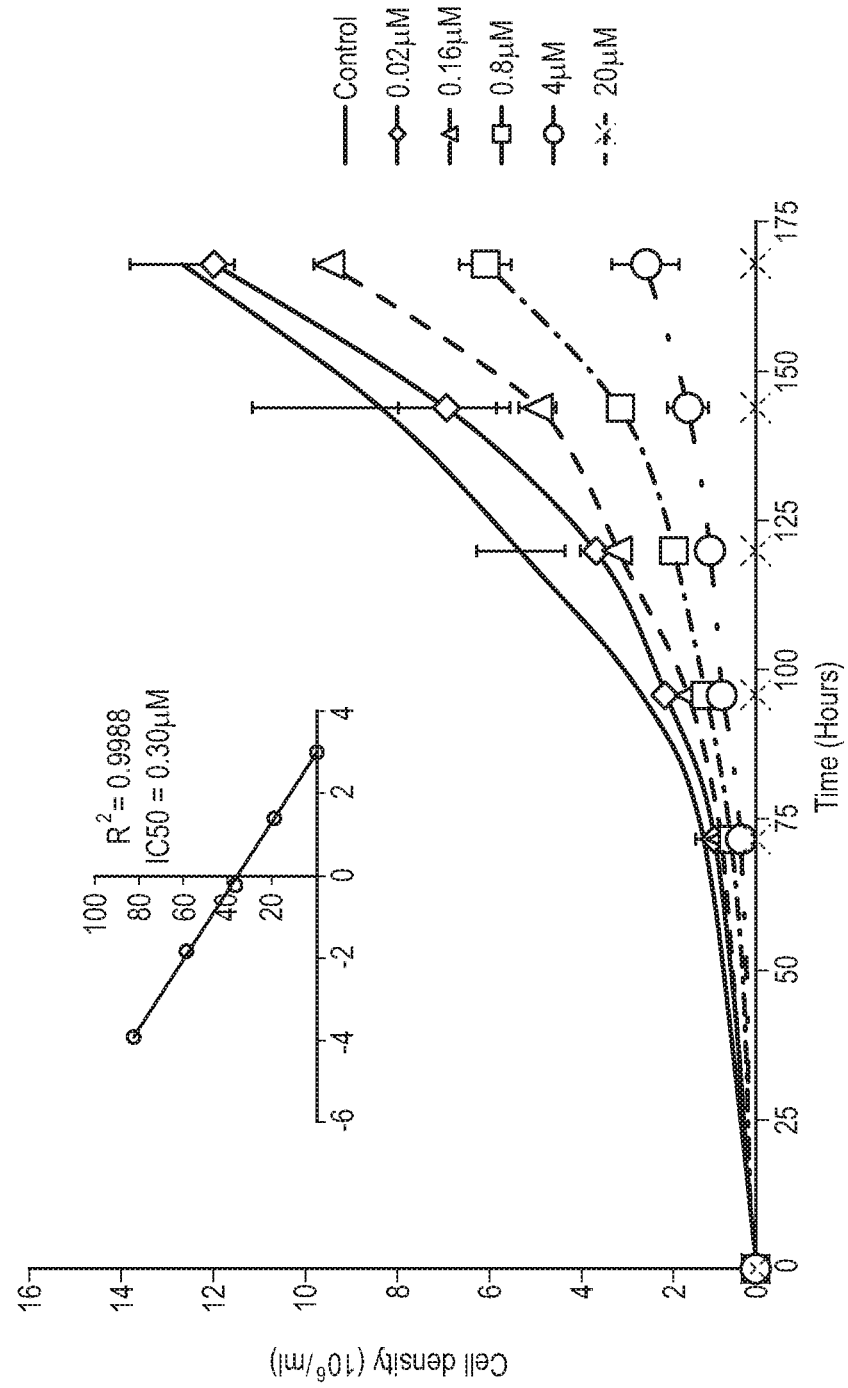
FIG. 3 shows the effect of CBDA on *D. discoideum* cell growth.

FIG. 3: Growth was measured over a seven day period in the presence of CBDA at concentrations ranging from 0.02 µM to 20 µM. A secondary plot of cell density at 168 hours was used to calculate an IC50 of 0.30 µM.

Figure 4:
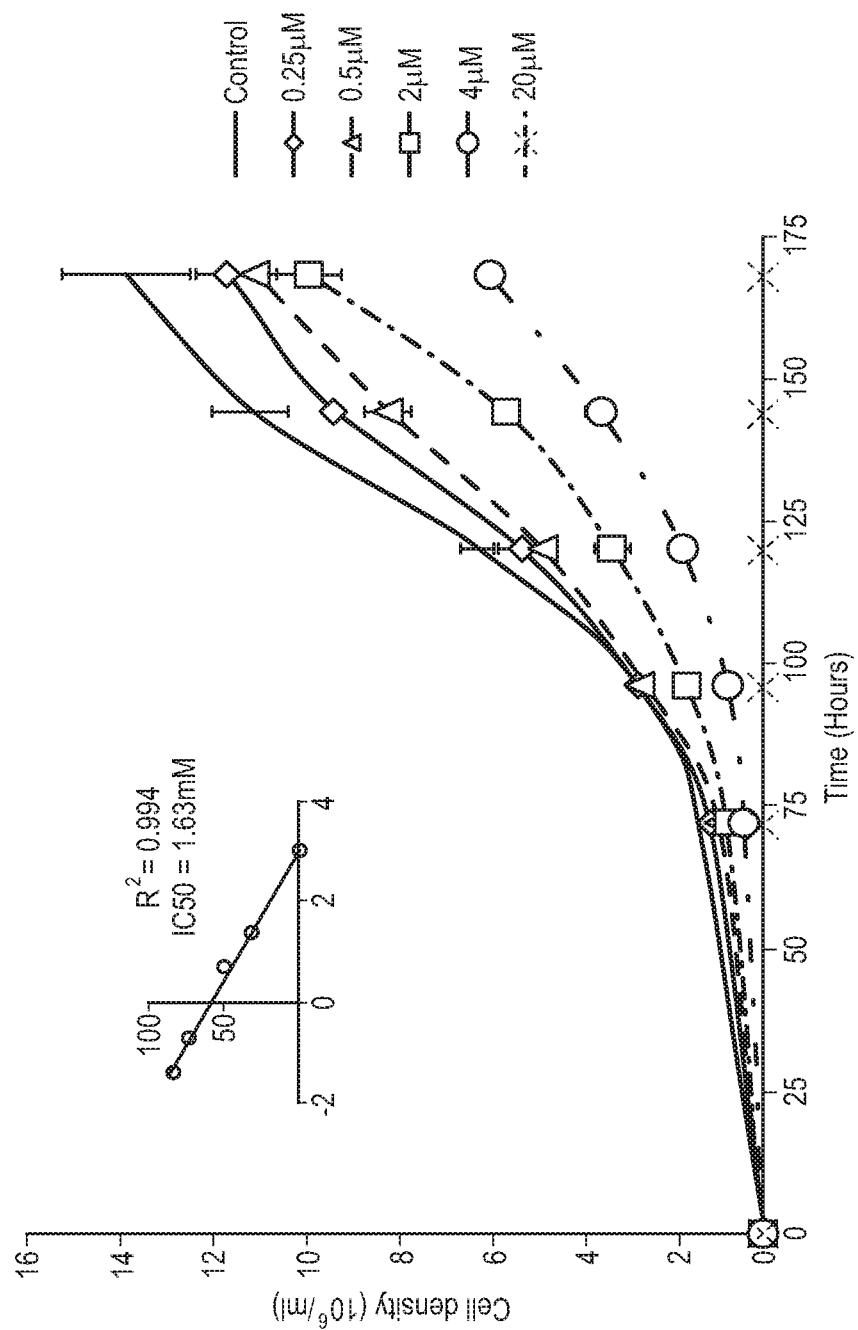
FIG. 4 shows the effect of CBD on *D. discoideum* cell growth.

FIG. 4: Growth was measured over a seven day period in the presence of CBD (from GW Pharmaceuticals) at concentrations ranging from 0.25 µM to 20 µM. A secondary plot of cell density at 144 hours was used to calculate an IC50 of 1.63 µM.

Figure 5:
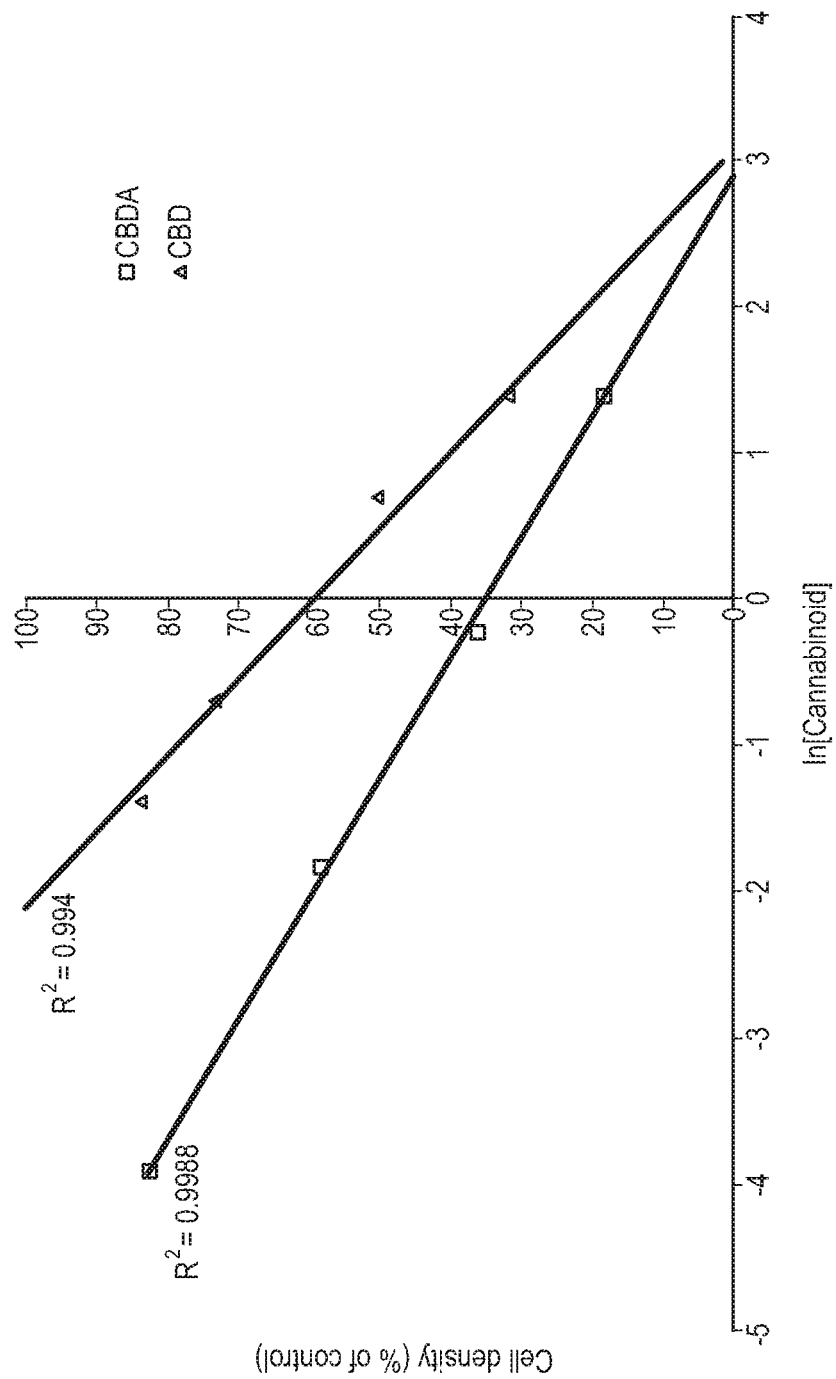
FIG. 5 shows secondary plots for the effect of CBDA and CBD on *D. discoideum* growth.

FIG. 5: Cannabinoids have a potency order of CBDA>CBD.

Figure 6:
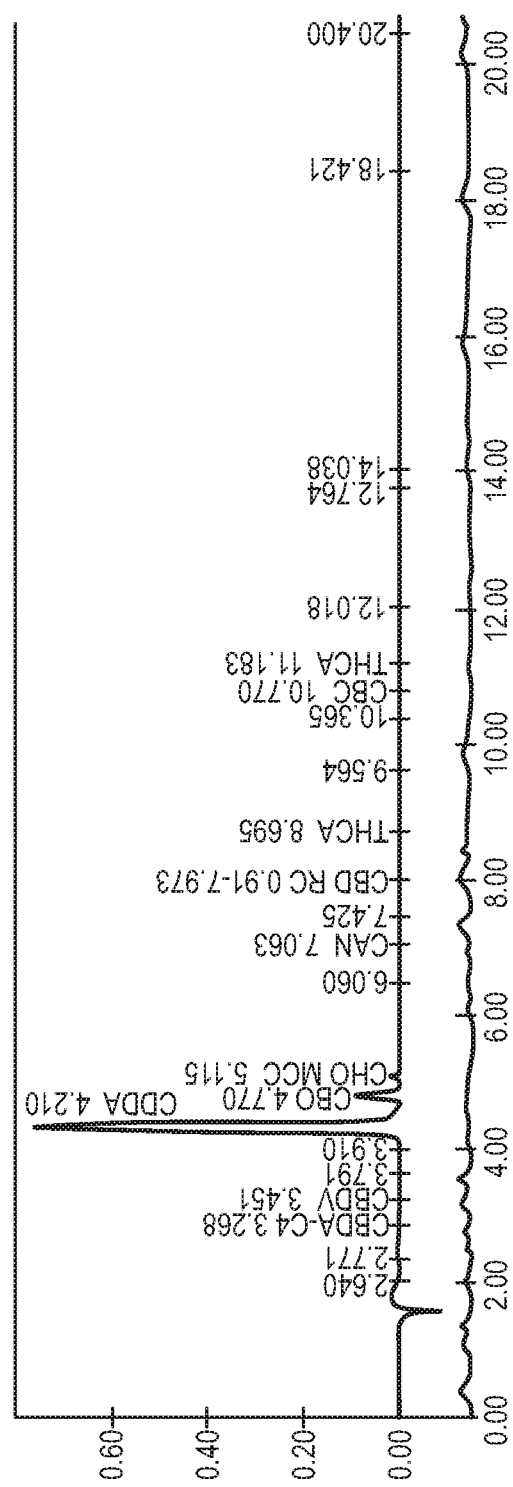
FIG. 6 shows the HPLC trace of the CBDA extract of Example 3.

FIG. 6: The CBDA botanical drub substance shown in the HPL trace comprised a CBDA content of 62.4% w/w and other cannabinoids measured included CBD—6.9% (w/w), THC—0.7% (w/w) and cannabichromene (CBC)—0.5% (w/w).

DETAILED DESCRIPTION

Example 1: An In Vivo Evaluation of CBDA in the Acute Pentylenetetrazole (Ptz) Model of Generalised Seizure Materials and Methods
Animals Adult male Wistar Kyoto rats were used in the acute PTZ model of seizure (>P24, 70-110 g). Animals were housed five per cage in a heat regulated room (21° C.) on a 12:12 h day/night cycle (lights on 0800) in 50% humidity and given ad libitum access to standard laboratory chow (PCD Mod C, Special Diet Services, Wiltham, UK) and water. All procedures were undertaken during white light hours.

Pharmaceutical Formulation

A PTZ (Sigma-Aldrich, Poole, UK) stock solution was made in 0.9% w/v NaCl for the experimental procedure. CBD (batch number, CBD-CG-1001; GW Pharmaceuticals, Salisbury, UK) and CBDA (batch number, CBDA040912; GW Pharmaceuticals) stocks were made in a 2:1:17 vehicle of ethanol, cremophor and saline.

Formulation analysis was undertaken to determine whether CBDA decarboxylated to CBD because of temperature and/or the excipients in the formulation. Analysis revealed CBDA was not converted to CBD during formulation. Therefore, CBDA was not modified during formulation, and a 2:1:17 ratio can be used in future investigations for this phytocannabinoid.

PTZ-Induced Model of Generalised Seizure

PTZ antagonises GABA inhibition via binding to the t-butyl-bicycl-phosphorothionate site of GABAA receptors. Moreover, this chemically-induced model can be indicative of effects against absence seizures. PTZ (90 mg/kg) was used to induce seizures in adult male Wistar rats (n=15 per group) with experiment dose randomised using a Latin square design. Animals were placed in their 6 L Perspex tanks and allowed to acclimatise to their environment for 10 min, before receiving one of the cannabinoid doses (see Table 5) in vehicle, or volume-matched dose of vehicle alone to serve as a negative control. 60 min after test compound or vehicle administration, animals were injected with PTZ (90 mg/kg, i.p.) to induce seizures and animal behaviour was recorded for 30 min.

TABLE 5

Doses of cannabinoid

| | Dose (mg/kg) | |
|---|---|---|
| | CBDA | CBD |
| Vehicle | — | — |
| CBDA | 10 | — |
| CBDA | 50 | — |
| CBDA | 100 | — |
| CBD | — | 100 |
| CBDA/CBD | 10 | 90 |

Videos of PTZ-induced seizures were scored offline with a standard seizure severity scale appropriate for generalised seizures (Table 6).

The human dose equivalent (HED) can be estimated using the following formula:

$$HED = \text{Animal dose (mg/kg) multiplied by } \frac{\text{Animal } K_m}{\text{Human } K_m}$$

The $K_m$ for a rat is 6 and the $K_m$ for a human is 37.
The $K_m$ for a dog (Example 3) is 20.
Thus a 10 mg/Kg dose in a rat would equate to a human dose of about 1.6 mg/kg. A 50 mg/kg dose in a rat would equate to a human dose of about 8.1 mg/kg. A 100 mg/kg dose in a rat would equate to a human dose of about 16.2 mg/kg.

TABLE 6

Seizure severity scoring scale.

| Seizure score | Behavioural expression | Righting reflex |
|---|---|---|
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |

Data Analysis

Videos of seizure behaviour generated from the custom built observational system were scored offline according to seizure scales appropriate for PTZ model (Table 6) using Observer Video-Pro software (Noldus, Wageningen, The Netherlands). For the PTZ model of seizure, intra- and inter-observer agreements of behaviour scoring were assessed using the reliability analysis function of the observer Video-Pro software: 1 s tolerance window; Cohen's Kappa coefficient ≥0.95.

Specific markers of seizure behaviour and development were assessed and compared between vehicle control and drug groups. The latency (s) to seizure onset and the percentage of animals that developed tonic-clonic seizures was noted (see Table 6). In addition, the maximum seizure severity and the percentage mortality in each group were determined for the acute PTZ model of generalised seizure.

Statistical Analysis

The effect of drug on latency to seizure onset and maximum seizure severity were assessed using Krustal-Wallis with post-hoc Mann-Whitney U-tests. Drug effects on the percentage of animals that developed tonic-clonic seizures and percentage mortality were assessed using Chi-squared with post-hoc Fisher exact tests. In all cases, $P \leq 0.05$ was considered significant.

Results

The objective of the present Example was to examine the anti-convulsant potential of CBDA in the PTZ-induced acute model of generalised seizure, with a comparator CBD dose. Additionally, CBD and CBDA in a ratio of 9:1 was included to investigate possible interactions between CBD and CBDA.

Cannabinoid treatment significantly reduced seizure severity in the acute PTZ-induced model of generalised seizure (FIG. 2. Panel A; H=14.31, $P \leq 0.05$), where 100 mg/kg CBDA ($P \leq 0.05$) and a CBD/CBDA ratio ($P \leq 0.05$) exhibited significant anti-convulsant effects vs vehicle control.

Mortality was significantly reduced (FIG. 2. Panel B; $X2(6)=30.51$, $P \leq 0.0001$) following administration of 100 mg/kg CBD ($P \leq 0.01$) and a trend towards a significant reduction for 100 mg/kg CBDA (P=0.0656) and a CBD/CBDA ratio (P=0.0656).

Cannabinoid treatment also significantly reduced incidence of tonic-clonic seizures (FIG. 2. Panel C; $X2(6)=17.178$, $P \leq 0.01$) where administration of 100 mg/kg of CBDA resulted in a trend towards a reduction in tonic-clonic seizures ($P \leq 0.1$).

Finally, analysis revealed cannabinoid administration significant affected latency to seizure onset in the PTZ-induced model (FIG. 2. Panel D; H=37.37, $P \leq 0.0001$), with 100 mg/kg CBD ($P \leq 0.05$), CBD/CBDA (9:1 ratio; $P \leq 0.05$) significantly increasing latency to onset. Whereas CBDA (100 mg/kg) showed a trend towards increasing the latency to seizure onset (P=0.0929).

Conclusions

As predicted by previous studies, CBD exerted anti-convulsant effects in this model of acute generalised seizure and so demonstrates the continued validity of the model to reveal anti-convulsant effects of plant cannabinoids.

Notably, in three of the four parameters measured CBDA produced significant anti-convulsant effects and were statistically more effective than CBD at an equivalent dose.

For example, Panel A of FIG. 2 describes the effect of CBDA and CBD on the seizure severity. The median score for the maximum seizure severity that the animals experienced with 100 mg/kg CBDA was 3 (Table 6—fully developed bilateral forelimb clonus, with righting reflex preserved) and the median for 100 mg/kg CBD was 5 (Table 6—fully developed tonic-clonic seizure, with righting reflex lost). This shows that CBDA was able to prevent the animals from suffering from more severe types of seizure than CBD was.

Panel C additionally demonstrates that CBDA at 100 mg/kg was able to prevent tonic-clonic seizures from developing in more animals compared to CBD at 100 mg/kg. Indeed the data for 100 mg/kg CBDA was the only statistically significant data in this parameter. This suggests that CBDA will be more effective than CBD at preventing or treating epilepsy, particularly tonic-clonic seizures from developing.

Co-administration of CBDA with CBD, in an exemplary 9:1 ratio, demonstrated that the combination was also effective as an anti-convulsant. Since the plant naturally produces CBDA and this can be decarboxylated, this opens up the possibility of using partially decarboxylated phytocannabinoids or extracts thereof, in given ratios. Such ratios may be beneficial for a number of reasons. These include targeting different types of seizures e.g. CBD for partial seizures and CBDA for generalised seizures may be beneficial based on their different activities in animal models of epilepsy. Also, the difference in the lipophilicity or bioavailability of the two compounds may enable combinations to be developed with different release profiles e.g. CBDA may be quicker acting than CBD and more bioavailable than CBD (see Example 3).

This Example demonstrates for the first time that the isolated or highly purified cannabinoid CBDA has anti-convulsant effects and as such further investigation in other models of seizure and epilepsy are warranted in order to determine the full extent of its efficacy.

In order to consider whether CBD and CBDA act by similar mechanisms and have similar potency the applicant conducted a study on a new model of *Dictyostelium discoideum*.

Example 2: Use of *Dictyostelium Discoideum* Model to Identify Molecular Targets of Cannabinoids and their Use in Epilepsy Introduction

*Dictyostelium discoideum* is an amoeba, listed by the US National Institute of Health as a biomedical model system (Williams et al. 2006). It has a cellular structure typical of eukaryotes, with nuclei, Golgi, mitochondria and endoplasmic reticulum and its haploid genome has been fully characterised and annotated (Dictybase.org) including descriptions of each protein, the phenotype of mutants lacking each protein and related published material. *D. discoideum* can be grown in liquid culture as single cells or allowed to progress into multi-cellular development upon starvation with the formation of a multi-cellular fruiting body.

*D. discoideum* has been developed to better understand the molecular mechanisms by which diverse drugs and chemicals exert their effects, to identify more potent or safer compounds, and to characterise the cellular role of human proteins This range of methodologies has enabled *D. discoideum* to be used as a valuable model in diverse areas in molecular pharmacology and pharmacogenetics. In these research areas, the primary target of either established or new pharmaceutical compounds is often unclear, and compounds often have off-target side effects that remain uncharacterised, and which may result in costly late-stage drug attrition and potentially affecting patient compliance.

In epilepsy research, *D. discoideum* has been used to identify molecular effects of valproic acid (Cunliffe et al 2015; Chang et al. 2012) and translated in vitro and in vivo mammalian models to demonstrate relevance to human health (Chang et al 2012, 2013, 2014). It is clear that *D. discoideum* can be used to identify clinically relevant therapeutic compounds for the treatment of epilepsy.

The present Example demonstrates the use of *D. discoideum* to identify the molecular mechanism(s) of action of two cannabinoids, (CBD and CBDA), with relevance to seizure control.

Materials and Methods
Growth Assays

Wild type (Ax2) *D. discoideum* cells were grown in shaking culture (in HL5 medium) for two days prior to growth assays. Cells (9900 in 495 μl of media) were added to each well of a 24 well plate and 5 μl of cannabinoid in DMSO (or DMSO only) was added to each well to achieve each described concentration (1% final DMSO concentration), and cells were maintained at 22° C. Cells were counted at 72 hours, and then every 24 hours. Quadruplicate repeats were used for each concentration.

Development Assays

Wild type (Ax2) *D. discoideum* cells were grown in HL5 shaking culture for two days prior to development assay. Cells were washed in phosphate buffer (KK2; 20 mM Potassium phosphate buffer, pH 6.1), and 1×10$^7$ cells were spread onto nitrocellulose filters (Millipore, Cork). Absorbent pads (Millipore, Cork), divided into quarters, were placed in 2 ml culture dishes and soaked with 0.5 ml KK2 containing the cannabinoids at 20 μM. 1 mM Valproic acid was used as a positive control while KK2 containing 1% DMSO was used as a solvent only control. Nitrocellulose filters containing cells were quartered and place upon absorbent pads and maintained in a humid environment at 22° C. for 24 h. Fruiting body morphology was recorded using a dissection microscope and camera.

Bioinformatic Analysis

The amino acid sequence for potential *H. sapien* protein targets of the cannabinoids listed were obtained from Uniprot (www.uniprot.org). Homology searches of the *D. discoideum* genome were carried out using the online Basic local alignment search (BLAST) algorithm available at dictybase.org. TMHMM server V. 2.0 transmembrane region predictor software was used to determine possible transmembrane regions within the *D. discoideum* orthologue proteins. Regions of the proteins containing highly conserved residues required for protein function were analysed by multiple sequence alignment using ClustalW2.

Bacterial Plate Screen

SM agar plates were made with the addition of CBDA or CBD to final concentrations of 12.3 μM and 16.7 μM respectively. Heat killed (75° C. for 30 minutes) *R. planticola* was spread onto the plates and ~50 wild-type AX2 cells were added and left to grow at 22° C. Plates were checked regularly for colonies.

Mutant REMI Library Screen

REMI library cells were grown in shaking culture (in HL5 medium) for two days prior to screening. Cells (25,000 in 2 ml of media) were added to each well of a 6 well plate and allowed to adhere for 20 minutes. The media from each well was replaced with media containing either: 4.88 μM CBDA or 9.47 μM CBD. Cells were screened in triplicate over a three week period, maintained at 22° C. with the media being replaced every two days. Potential resistant mutant colonies were isolated and transferred to bacterial plates. Isogenic cell lines were established from individual colonies on the bacterial plates.

Confirmation of Individual Mutant Resistance:

Clonal cells isolated from the library screen were grown in liquid media (HL5 medium) to produce a confluent 10 cm plate. Cells (10,000 in 495 μl of media) were added to each well of a 24 well plate and 5 μl of cannabinoid in DMSO was added to each well to achieve either 4.88 μM CBDA or 9.47 μM CBD (1% final DMSO concentration), cells were maintained at 22° C. Cells were monitored over a one week for their sensitivity to the two cannabinoids.

Results
Growth Assays

It first needed to be determined if *D. discoideum* growth was sensitive to the cannabinoids: cannabidiolic acid (CBDA) and cannabidiol (CBD). In these experiments, *D. discoideum* were exposed to a range of concentrations of each cannabinoid during growth in still culture over a one week period. All two cannabinoids inhibited *D. discoideum* cell growth in a dose dependent manner (FIGS. 3 to 5).

The growth inhibitory constant (IC50) for CBDA was 0.30 μM (FIG. 3), with 0.08 μM significantly inhibiting cell growth (P<0.05) and 20 μM blocking growth.

The growth inhibitory constant (IC50) for CBD was 1.63 uM (FIG. 4), with 0.5 μM significantly inhibiting cell growth (P<0.05) and 20 μM blocking growth.

Comparison of all two cannabinoids IC50 values suggests CBDA is the most potent, with CBD showing an 8.7-fold reduction in potency. Thus the order of potency for cannabinoids on *D. discoideum* cell growth is CBDA>CBD (FIG. 5).

Development Assays

The effects that CBDA and CBD had upon *D. discoideum* development were investigated. This was achieved by placing cells in a nutrient depleted environment in the presence of CBDA or CBD at concentrations that block cell growth (20 μM).

Cell development on a nitrocellulose filter over a 24 hour period in the absence of cannabinoids gave rise to fruiting bodies consisting of spore heads held above substrata by stalks. This developmental morphology is known to be blocked by the widely used anti-epileptic, valproic acid (1 mM), where cells were able to aggregate but unable to undergo development to form fruiting bodies.

In contrast, *D. discoideum* cells treated with CBDA or CBD (20 μM) were able to aggregate and develop to form mature fruiting bodies.

Bioinformatic Analysis

Known targets of CBDA and CBD in *H. sapiens* were then sought in order to identify potential orthologues within the *D. discoideum* genome. From current literature, 21 possible mammalian targets of CBDA and CBD have been published. Using human protein sequences corresponding each potential target, in combination with BLAST analysis, the *D. discoideum* genome was searched for orthologous targets. Using this approach, 10 possible *D. discoideum* orthologues were identified. Based upon similarity of protein sequence and size, and conservation of catalytic sites and motifs, three proteins have been identified for further study:

1: Equilibrative Nucleoside Transporter 1 (ENT1). This protein is a potential target for CBD and plays a role in adenosine transport. *D. discoideum* has three possible ENT1 orthologues, and all three have a putative multiple transmembrane structure found in the *H. sapiens* protein. The three *D. discoideum* orthologues are 522, 482 and 430 aa in size, similar to the 456 aa *H. sapiens* ENT1 protein, and contain a highly conserved motif located within first transmembrane region. This motif is found within this protein from many other species.

2: Monoacylglyceride lipase alpha (MAGLa). This protein is involved in the endocannabinoid system. *D. discoideum* has one possible MAGLa orthologue. This orthologue is 409 aa, of similar size to the 303 aa *H. sapien* MAGLA protein. Both the *D. discoideum* and *H. sapiens* proteins have a conserved catalytic serine, aspartate and histidine residue that are important in enzymatic function that are widely conserved in many other species.

3: Diacylglycerol lipase alpha (DAGLa). This protein is involved in the endocannabinoid system. *D. discoideum* has three possible orthologues. The three *D. discoideum* orthologues are 938, 856 and 826 aa in size, slightly smaller than the 1042 aa *H. sapiens* DAGLa protein. All three *D. discoideum* orthologues have the same conserved serine and aspartate residues that are important in catalytic function, and these are widely conserved in many other species.

Bacterial Plate Screen

It was determined if *D. discoideum* growth upon *R. planticola* bacterial plates was a viable method in which resistant REMI mutant library cells could be isolated. Wild-type AX2 cells were grown upon heat killed *R. planticola* SM agar plates. Each SM agar plate contained CBDA or CBD at a final concentration of 12.3 µM and 16.7 µM respectively. Following incubation for 4 days, plates were assessed for cell survival (colony growth). No difference in colony number was found for every cannabinoid compared to control (solvent only).

Mutant REMI Library Screen

Mutants were then identified within the library that showed resistance to the cannabinoids during growth in liquid culture. The library cells were grown over a three week period in the presence of 4.88 µM CBDA or 9.47 µM CBD. After a two week period colonies of partially resistant cells were visible in library-derived plates. Partially resistant cells were transferred to bacterial plates and passaged to ensure each mutant was isogenic.

Confirmation of Individual Mutant Resistance

The resistance of each cell line was confirmed. All cell lines were treated with either: CBDA or CBD at a final concentration of 4.88 µM and 9.47 µM respectively and assessed after one week. Isogenic cell lines showed some overlap of resistance to the different cannabinoids. Mutant cells were shown to have 3 basic phenotypes to each cannabinoid, classified as showing no resistance, weak resistance or partial resistance. Mutant cells were also found to have either resistance to one cannabinoid or to multiple cannabinoids.

Conclusions

The development of cannabinoids as novel therapeutic treatments for epilepsy provides an exciting new field of research, with real potential for improving health. A comprehensive understanding of the mechanisms of action and relative potency of these compounds are essential for therapeutic development, to understand both how the compounds block seizures and potential side effects. Traditional approaches to identify these mechanisms are very complex and slow. As an alternative approach, *D. discoideum* has been used to identify mechanism of a widely used treatment, valproic acid, which has been verified in mammalian in vivo models.

In this current study, it has been demonstrated that two cannabinoids, CBDA, and CBD block *D. discoideum* growth. Concentrations that affect growth are in the low µM range and are equivalent to the concentrations shown to be anti-convulsant in animal models of seizure. This suggests that targets for all two cannabinoids are present in the *D. discoideum* genome. This also suggests that the *D. discoideum* targets have a similar sensitivity to the cannabinoids that shown in mammalian models.

The growth inhibitory effect can then be employed in an unbiased screen to identify these cannabinoid targets. Using a library of insertional mutants, a pool of mutants can be grown in the presence of each cannabinoid over a 21 day period. Mutants with insertions into genes encoding cannabinoid targets are likely to show resistance to this growth inhibition and thus out-compete sensitive cells during the screen. Identification of insertionally-inactivated genes in cannabinoid resistant colonies will identify molecular targets (and mechanism) of these cannabinoids in an unbiased approach. This screening approach in *D. discoideum* has been used to identify targets and mechanisms of a range of compounds.

*D. discoideum* is also widely used as a development model, where the formation of a fruiting body involves cell aggregation and differentiation. Pharmacological studies have used this developmental process to identify drug mechanisms. In relation to the cannabinoids studied here, all two compounds had no effect on *D. discoideum* development, at concentrations shown to block growth. This firstly suggests that the block in *D. discoideum* growth is not toxic, since cells can develop, and thus that cannabinoid targets are likely to be involved in blocking cell growth or division (cytokinesis). This also suggests that *D. discoideum* development cannot be used to further study these compounds. In combination with an unbiased approach to identifying cannabinoid targets, *D. discoideum* also provides a useful model to investigate known mammalian targets.

It was found that a total of 25 mutant cell lines showed resistance to growth inhibition. The range of resistant phenotypes to different cannabinoids suggests that there are multiple genes involved Example 3 Comparison of PK Data for CBD and CBDA from Toxicological Studies in Dogs The objective of the studies was to determine the toxicity of CBD (in the form of a substantially pure compound—greater than 95% purity) and CBDA (in the form of a botanical drug substance—greater than 60% CBDA w/w of the total extract and greater than 85% w/w of the total cannabinoid content) following daily oral (gavage) administration to the dog.

This study was designed to meet the known requirements of European Directive 2001/83/EC and all subsequent amendments together with any relevant International Conference on Harmonisation (ICH) guidelines.

Blood samples for toxicokinetics (0.5 mL nominal) were taken from all animals on Day 1 at 0.5, 1, 2, 4, 6 and 24 hours after the dosing of 100 mg/kg of either CBD or CBDA to the animals.

Samples were taken from the jugular vein into lithium heparin. Samples were mixed gently by hand then continuously for at least 2 minutes on automatic mixer and placed in a Kryorack until centrifugation, which was carried out at approximately 4° C. as soon as practicable. The resultant plasma was separated under low light conditions, transferred to uniquely labelled clear glass vials, placed in light proof boxes and frozen immediately at <−50° C.

Toxicokinetic parameters measured included $C_{max}$ (ng/mL), $T_{max}$ (h) and $AUC_{0-t}$ (h*ng/mL) and the results are illustrated in Table 7 for CBDA, Table 8 for CBD (males), Table 9 for CBD (females) and the comparative $C_{max}$ and $AUC_{0-t}$ are shown in Table 10 for males and Table 11 for females.

Results

TABLE 7

Mean Toxicokinetic Parameters of CBDA are presented below:

| | | n = 3 Dose of CBDA BDS (mg CBDA/kg/day) | | | | | |
|---|---|---|---|---|---|---|---|
| | | 50 | | 100 | | 200 | |
| Parameter[a] | Period | Males | Females | Males | Females | Males | Females |
| $AUC_{0-t}$ | Day 1 | 55600 | 149000 | 80500 | 179000 | 269000 | 172000 |
| (h · ng/mL) | Day 28 | 71600 | 64100 | 116000 | 159000 | 94700 | 156000 |
| Cmax | Day 1 | 19100 | 21100 | 24900 | 38600 | 35000 | 27100 |
| (ng/mL) | Day 28 | 15700 | 15000 | 23400 | 32500 | 17700 | 35900 |
| Tmax | Day 1 | 1 | 3 | 1.3 | 1.7 | 2.7 | 1.7 |
| (h) | Day 28 | 1.7 | 2 | 1.5 | 1.7 | 9 | 1.3 |

[a]Results are reported as mean unless stated otherwise

TABLE 8

| Subject | $C_{max}$ (ng/mL) | $t_{max}$ (h) | $t_{1/2}$ (h) | $AUC_{0-t}$ (h * ng/mL) | $AUC_{0-inf}$ (h * ng/mL) | $AUC_{ex}$ (%) | CL/F (mL/min/kg) | $V_z/F$ (L/kg) |
|---|---|---|---|---|---|---|---|---|
| 15 | 4570 | 6.0 | 7.7 | 51800 | 60500 | 14.3 | 27.5 | 18.4 |
| 16 | 3620 | 4.0 | 5.4 | 33000 | 35400 | 6.8 | 47.1 | 21.9 |
| 17 | 1400 | 6.0 | 8.5 | 17200 | 20300 | 15.1 | 82.1 | 60.5 |
| 18 | 2430 | 4.0 | 5.7 | 28700 | 31100 | 7.9 | 53.6 | 26.2 |
| 19 | 3090 | 8.0 | n.d. | 26400 | n.d. | n.d. | n.d. | n.d. |
| 20 | 3960 | 6.0 | 8.6 | 47300 | 55300 | 14.5 | 30.1 | 22.3 |
| N | 6 | 6 | 5 | 6 | 5 | 5 | 5 | 5 |
| Mean | 3180 | n.d. | 7.2 | 34100 | 40500 | 11.7 | 48.1 | 29.9 |
| SD | 1140 | n.d. | 1.5 | 13100 | 16900 | 4.0 | 22.0 | 17.3 |
| Min | 1400 | 4.0 | 5.4 | 17200 | 20300 | 6.8 | 27.5 | 18.4 |
| Median | 3360 | 6.0 | 7.7 | 30800 | 35400 | 14.3 | 47.1 | 22.3 |
| Max | 4570 | 8.0 | 8.6 | 51800 | 60500 | 15.1 | 82.1 | 60.5 |
| Geometric Mean | 2970 | n.d. | 7.0 | 31900 | 37600 | 11.1 | 44.4 | 27.0 |
| CV % Geometric Mean | 44.8 | n.d. | 23 | 42.2 | 46.9 | 39.6 | 46.9 | 49.5 |

TABLE 9

| Subject | $C_{max}$ (ng/mL) | $t_{max}$ (h) | $t_{1/2}$ (h) | $AUC_{0-t}$ (h * ng/mL) | $AUC_{0-inf}$ (h * ng/mL) | $AUC_{ex}$ (%) | CL/F (mL/min/kg) | $V_z/F$ (L/kg) |
|---|---|---|---|---|---|---|---|---|
| 115 | 655 | 2.0 | 8.4 | 3000 | 3280 | 8.7 | 508 | 367 |
| 116 | 2520 | 2.0 | 6.6 | 20000 | 22400 | 10.6 | 74.5 | 42.9 |
| 117 | 1900 | 8.0 | n.d. | 22600 | n.d. | n.d. | n.d. | n.d. |
| 118 | 411 | 1.0 | 4.5 | 2540 | 2640 | 3.7 | 632 | 247 |
| 119 | 3270 | 8.0 | n.d. | 32400 | n.d. | n.d. | n.d. | n.d. |
| 120 | 3780 | 6.0 | 4.7 | 31300 | 32800 | 4.5 | 50.8 | 20.8 |
| N | 6 | 6 | 4 | 6 | 4 | 4 | 4 | 4 |
| Mean | 2090 | n.d. | 6.1 | 18600 | 15300 | 6.9 | 316 | 169 |
| SD | 1370 | n.d. | 1.8 | 13200 | 14800 | 3.3 | 297 | 167 |
| Min | 411 | 1.0 | 4.5 | 2540 | 2640 | 3.7 | 50.8 | 20.8 |
| Median | 2210 | 4.0 | 5.7 | 21300 | 12800 | 6.6 | 291 | 145 |
| Max | 3780 | 8.0 | 8.4 | 32400 | 32800 | 10.6 | 632 | 367 |
| Geometric Mean | 1590 | n.d. | 5.9 | 12300 | 8930 | 6.3 | 187 | 94.8 |
| CV % Geometric Mean | 113 | n.d. | 30 | 172 | 208 | 54.2 | 208 | 238 |

TABLE 10

|  | CBDA (100 mg/kg) | CBD (100 mg/kg) |
|---|---|---|
| Cmax | 24,900 | 3180 |
| $AUC_{0-t}$ | 80,500 | 34,100 |

TABLE 11

|  | CBDA (100 mg/kg) | CBD level (100 mg/kg) |
|---|---|---|
| Cmax | 38,600 | 2090 ng/mL |
| $AUC_{0-t}$ | 179,000 | 18,600 ng/mL * hr |

Conclusions:

It will be apparent from the comparative Tables 10 and 11 that an equivalent amount of CBDA to CBD results in $C_m$, and $AUC_{04}$ values which are very significantly higher (by an order of magnitude) than that of CBD, suggesting that the CBDA is acting more quickly and is more bioavailable than the CBD. This has significant implications/benefits when it comes to treating patients.

OVERALL CONCLUSION

To summarise, the data presented in Examples 1, 2, and 3 demonstrates that:

CBDA has anticonvulsant effects in a mammalian model of epilepsy and is effective in treating generalised seizures, more particularly, tonic-clonic seizures. Indeed, this compound appears more effective than CBD in many of the parameters tested.

CBDA is significantly more potent than CBD upon growth of *D. discoideum*; and CBDA acts more quickly and is more bioavailable than CBD.

These findings are of great significance as they demonstrate that CBDA offers an alternative anti-convulsant to CBD. The finding that CBDA is more potent and more bioavailable than CBD means that a smaller daily dose of the active ingredient may be used in the treatment of epilepsy. In this regard, it appears from Example 3, that doses of less than 400 mg and possibly doses of as little as from 1 mg-100 mg, might be used to treat human subjects based on the PK and $AUC_{0-t}$ data of Example 3. In this regard, a typical adult patient might weigh 60 kg and thus, a daily dose for such a patient might be from 0.016 mg/kg to 1.6 mg/kg.

REFERENCES

Ames F R and Cridland S (1986). "Anticonvulsant effects of cannabidiol." S Afr Med J 69:14.
Chang, P., et al. "The antiepileptic drug valproic acid and other medium-chain fatty acids acutely reduce phosphoinositide levels independently of inositol in *Dictyostelium*." Dis. Model. Mech. 5.1 (2012): 115-24.
Chang, P., et al. "Seizure control by ketogenic diet-associated medium chain fatty acids." Neuropharmacology 69 (2013): 105-14.
Chang, P., M. C. Walker, and R. S. Williams. "Seizure-induced reduction in PIP3 levels contributes to seizure-activity and is rescued by valproic acid." Neurobiol. Dis. 62 (2014): 296-306.
Consroe P, Martin P, Eisenstein D. (1977). "Anticonvulsant drug antagonism of delta-9-tetrahydrocannabinol induced seizures in rabbits." Res Commun Chem Pathol Pharmacol. 16:1-13
Consroe P, Benedicto M A, Leite J R, Carlini E A, Mechoulam R. (1982). "Effects of cannabidiol on behavioural seizures caused by convulsant drugs or current in mice." Eur J Pharmaco. 83: 293-8
Cunha J M, Carlini E A, Pereira A E, Ramos O L, Pimental C, Gagliardi R et al. (1980). "Chronic administration of cannabidiol to healthy volunteers and epileptic patient." Pharmacology. 21:175-85
Cunliffe, Baines, Giachello, Lin, Morgan, Reuber, Russell, Walker and Williams Epilepsy "Research Methods Update: Understanding the causes of epileptic seizures and identifying new treatments using non-mammalian model organisms". Seizure: European Journal of Epilepsy. 24C (2015):44-51.
Eadie, M J (December 2012). "Shortcomings in the current treatment of epilepsy." *Expert Review of Neurotherapeutics* 12 (12): 1419-27.
Kwan P, Arzimanoglou A, Berg A T, Brodie M J, Hauser W A, Mathern G, Moshe S L, Perucca E, Wiebe S, French J. (2009) "Definition of drug resistant epilepsy: Consensus proposal by the ad hoc Task Force of the ILAE Commission on Therapeutic Strategies." *Epilepsia*.
Mechoulam R and Carlini E A (1978). "Toward drugs derived from *cannabis*." Die naturwissenschaften 65:174-9.
Porter B E, Jacobson C (December 2013). "Report of a parent survey of cannabidiol-enriched *cannabis* use in paediatric treatment resistant epilepsy" Epilepsy Behaviour. 29(3) 574-7
Thurman, D J; Beghi, E; Begley, C E; Berg, A T; Buchhalter, J R; Ding, D; Hesdorffer, D C; Hauser, W A; Kazis, L; Kobau, R; Kroner, B; Labiner, D; Liow, K; Logroscino, G; Medina, M T; Newton, C R; Parko, K; Paschal, A; Preux, P M; Sander, J W; Selassie, A; Theodore, W; Tomson, T; Wiebe, S; ILAE Commission on, Epidemiology (September 2011). "Standards for epidemiologic studies and surveillance of epilepsy." *Epilepsia*. 52 Suppl 7: 2-26
Williams, R. S., et al. "Towards a molecular understanding of human diseases using *Dictyostelium discoideum*." Trends Mol. Med. 12.9 (2006): 415-24.

The invention claimed is:

1. A method of treating epilepsy in a subject, comprising administering to the subject a therapeutically effective amount of cannabidiolic acid (CBDA), wherein the CBDA is in the form of a highly purified extract of *cannabis* such that the CBDA is present at greater than 95% of the total extract (w/w) or is synthetically produced.

2. The method according to claim 1, wherein the epilepsy is a generalized epilepsy.

3. The method according to claim 1, wherein the epilepsy is characterized by tonic-clonic seizures.

4. The method according to claim 1 wherein the therapeutically effective amount is at least 0.1 mg.

5. The method according to claim 1, wherein the highly purified extract comprises less than 1% (w/w) tetrahydrocannabinol (THC) or tetrahydrocannabinolic acid (THCA).

6. The method according to claim 1, wherein the CBDA is administered concomitantly with one or more other cannabinoids.

7. The method according to claim 6, wherein the one or more other cannabinoids is cannabidiol (CBD).

8. The method according to claim 7, wherein the CBDA:CBD ratio is in the range of from 9:1 to 1:9 (CBDA:CBD).

9. The method according to claim 1, wherein the CBDA is administered concomitantly with one or more other anti-epileptic drugs (AED).

10. The method according to claim 1, wherein the CBDA is administered at a dose of less than 400 mg.

11. The method according to claim 10, wherein the CBDA is administered at a dose of from 1 mg to 100 mg.

12. The method according to claim 1, wherein the CBDA is in the form of a highly purified extract of *cannabis* such that the CBDA is present at greater than 98% of the total extract (w/w).

13. The method according to claim 7, wherein the CBD is in the form of a highly purified extract of *cannabis* such that the CBD is present at greater than 95% of the total extract (w/w).

14. The method according to claim 7, wherein the CBD is in the form of a highly purified extract of *cannabis* such that the CBD is present at greater than 98% of the total extract (w/w).

15. The method according to claim 9, wherein the one or more AED is selected from the group consisting of: clobazam; clonazepam, levetiracetam; topiramate; stiripentol; phenobarbital; lacosamide; valproic acid; and zonisamide.

16. The method of claim 1, wherein said administering reduces seizure severity.

17. The method of claim 1, wherein said administering reduces the incidence of seizures.

18. The method of claim 17, wherein said administering reduces the incidence of tonic-clonic seizures.

19. The method of claim 1, wherein said administering increases latency to seizure onset.

* * * * *